United States Patent
Schendel et al.

(10) Patent No.: US 9,409,969 B2
(45) Date of Patent: Aug. 9, 2016

(54) REPERTOIRE OF ALLO-RESTRICTED PEPTIDE-SPECIFIC T CELL RECEPTOR SEQUENCES AND USE THEREOF

(75) Inventors: Dolores J. Schendel, Munich (DE); Susanne Wilde, Munich (DE); Bernhard Frankenberger, Munich (DE); Wolfgang Uckert, Berlin (DE)

(73) Assignees: Helmholtz Zentrum München Deutsches Forschungszentrum für Gesundheit und Umwelt (GmbH), Neuherberg (DE); MAX-DELBRUECK-CENTRUM FUER MOLEKULARE MEDIZIN, Berlin (DE)

( * ) Notice: Subject to any disclaimer, the term of this patent is extended or adjusted under 35 U.S.C. 154(b) by 419 days.

(21) Appl. No.: 13/148,653

(22) PCT Filed: Feb. 9, 2010

(86) PCT No.: PCT/EP2010/051565
§ 371 (c)(1),
(2), (4) Date: Nov. 28, 2011

(87) PCT Pub. No.: WO2010/089412
PCT Pub. Date: Aug. 12, 2010

(65) Prior Publication Data
US 2012/0128704 A1   May 24, 2012

Related U.S. Application Data

(60) Provisional application No. 61/150,934, filed on Feb. 9, 2009.

(51) Int. Cl.
*C07H 21/04* (2006.01)
*C07K 14/705* (2006.01)

(52) U.S. Cl.
CPC ................ *C07K 14/70503* (2013.01)

(58) Field of Classification Search
None
See application file for complete search history.

(56) References Cited

U.S. PATENT DOCUMENTS

| 4,703,004 A | 10/1987 | Hopp et al. |
| 4,851,341 A | 7/1989 | Hopp et al. |
| 5,906,936 A | 5/1999 | Eshhar et al. |

FOREIGN PATENT DOCUMENTS

| WO | WO-97/32603 A1 | 9/1997 |
| WO | WO 97/32603 A1 | 9/1997 |
| WO | WO-2007/065957 A2 | 6/2007 |
| WO | WO 2007/065957 A2 | 6/2007 |
| WO | WO 2007/100568 A2 | 9/2007 |
| WO | WO-2008/039818 A2 | 4/2008 |
| WO | WO 2008/039818 A2 | 4/2008 |

OTHER PUBLICATIONS

Janeway et al., Immunobiology, 5th Ed., Garland Science, pp. 106-108 and 260-263, (2001).*
Garcia et al., Cell, vol. 122, 333-336, Aug. 12, 2005.*
Portolano et al., J Immunol. Feb. 1, 1993;150(3):880-7.*
Dissertation of Elisa Kieback, Oct. 23, 2008, pp. 1-101.*
The Memorandum from Deputy Commissioner for Patent Examination Policy Andrew H. Hirshfeld, dated Mar. 4, 2014, 19 pages in total with first page not numbered.*
"Evaluating subject Matter Eligibility Under 35 U.S.C. § 101," Mar. 19, 2014 update, pp. 1-93.*
Polic et al. (pnas, 8744-8749, Jul. 17, 2001, vol. 98, No. 15).*
Roszkowski, J., et al., "Simultaneous Generation of CD8+ and CD4+ Melanoma-Reactive T Cells by Retroviral-Mediated Transfer of a Single T-Cell Receptor," *Cancer Research*, vol. 65(4), pp. 1570-1576 (Feb. 15, 2005).
Savage, P., et al., "Use of B cell-bound HLA-A2 class I monomers to generate high-avidity, allo-restricted CTLs against the leukemia-associated protein Wilms tumor antigen," *Blood*, vol. 103(12), pp. 4613-4615 (Jun. 15, 2004).
Javorovic et al., "Inhibitory effect of RNA pool complexity on stimulatory capacity of RNA-pulsed dendritic cells," J Immunother. 31(1):52-62 (2008).
Morgan et al., "Cancer regression in patients after transfer of genetically engineered lymphocytes," Science 314(5796): 10 pages (2006).
Morris et al., "Generation of tumor-specific T-cell therapies," Blood Rev. 20(2):61-9 (2006).
Roszkowski et al., "CD8-independent tumor cell recognition is a property of the T cell receptor and not the T cell," J Immunol. 170(5):2582-9 (2003).
Schumacher, "T-cell-receptor gene therapy," Nat Rev Immunol. 2(7):512-9 (2002).
Sommermeyer et al., "Designer T cells by T cell receptor replacement," Eur J Immunol. 36(11):3052-9 (2006).
Sørensen et al., "A survivin specific T-cell clone from a breast cancer patient display universal tumor cell lysis," Cancer Biol Ther. 7(12):1885-7 (2008).
Visseren et al., "Affinity, specificity and T-cell-receptor diversity of melanoma-specific CTL generated in vitro against a single tyrosinase epitope," Int J Cancer 72(6):1122-8 (1997).
Wölfl et al., "Quantitation of MHC tetramer-positive cells from whole blood: evaluation of a single-platform, six-parameter flow cytometric method," Cytometry A. 57(2):120-130 (2004).

* cited by examiner

*Primary Examiner* — Zachary Skelding
(74) *Attorney, Agent, or Firm* — Clark & Elbing LLP

(57) ABSTRACT

The present invention is directed to a kit-of-parts or composition containing nucleic acid sequences coding for high-avidity, allo-restricted TCR, wherein the TCR are independently directed against the tyrosinase antigen, the melan-A antigen and the survivin antigen. The invention is further directed to a kit-of-parts or composition containing at least three groups of transgenic lymphocytes transformed with vectors coding for TCR against said antigens. Furthermore, the present invention provides a pharmaceutical composition and its use in the treatment of diseases involving malignant cells expressing said tumor-associated antigens. The invention further relates to a nucleic acid molecule coding for a TCR that recognizes the survivin antigen, a TCR encoded thereby and a T cell expressing said TCR. Further, the invention discloses a vector, a cell and a pharmaceutical composition encoding/containing same and their use in the treatment of diseases involving malignant cells expressing survivin.

13 Claims, 3 Drawing Sheets

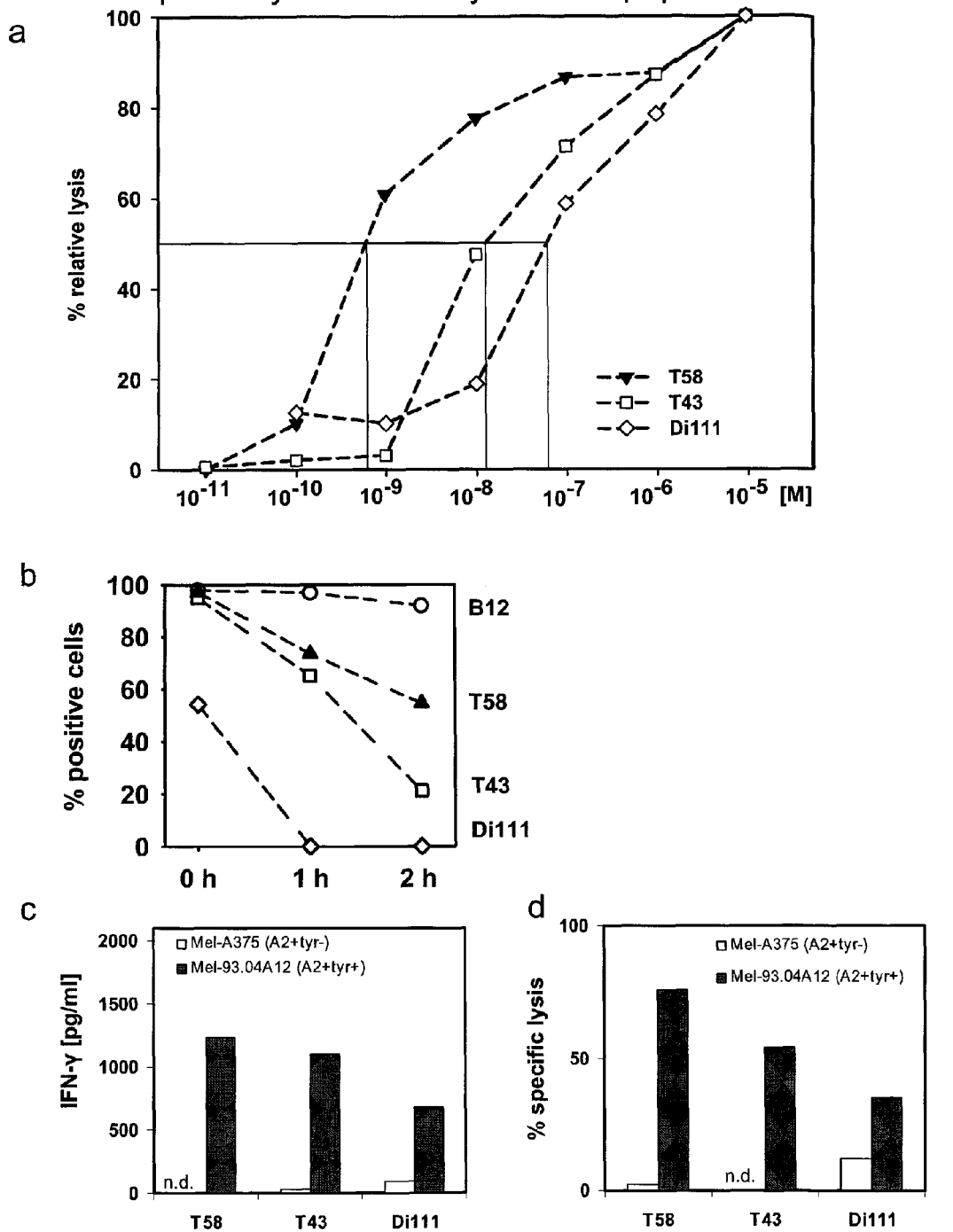
Figure 1: Allo-restricted T cell clones
Specificity: HLA-A2 + tyrosinase-peptide YMDGTMSQV

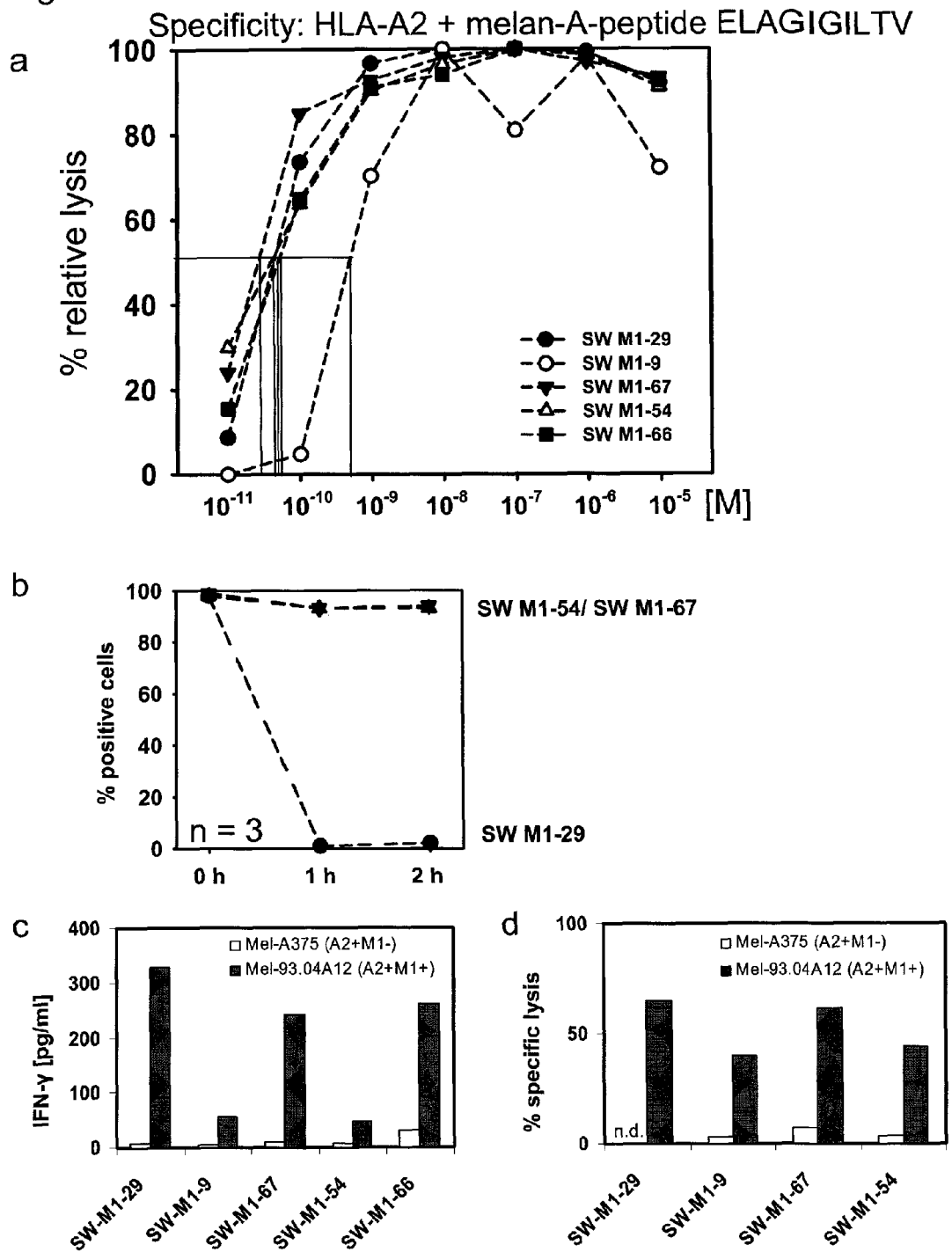

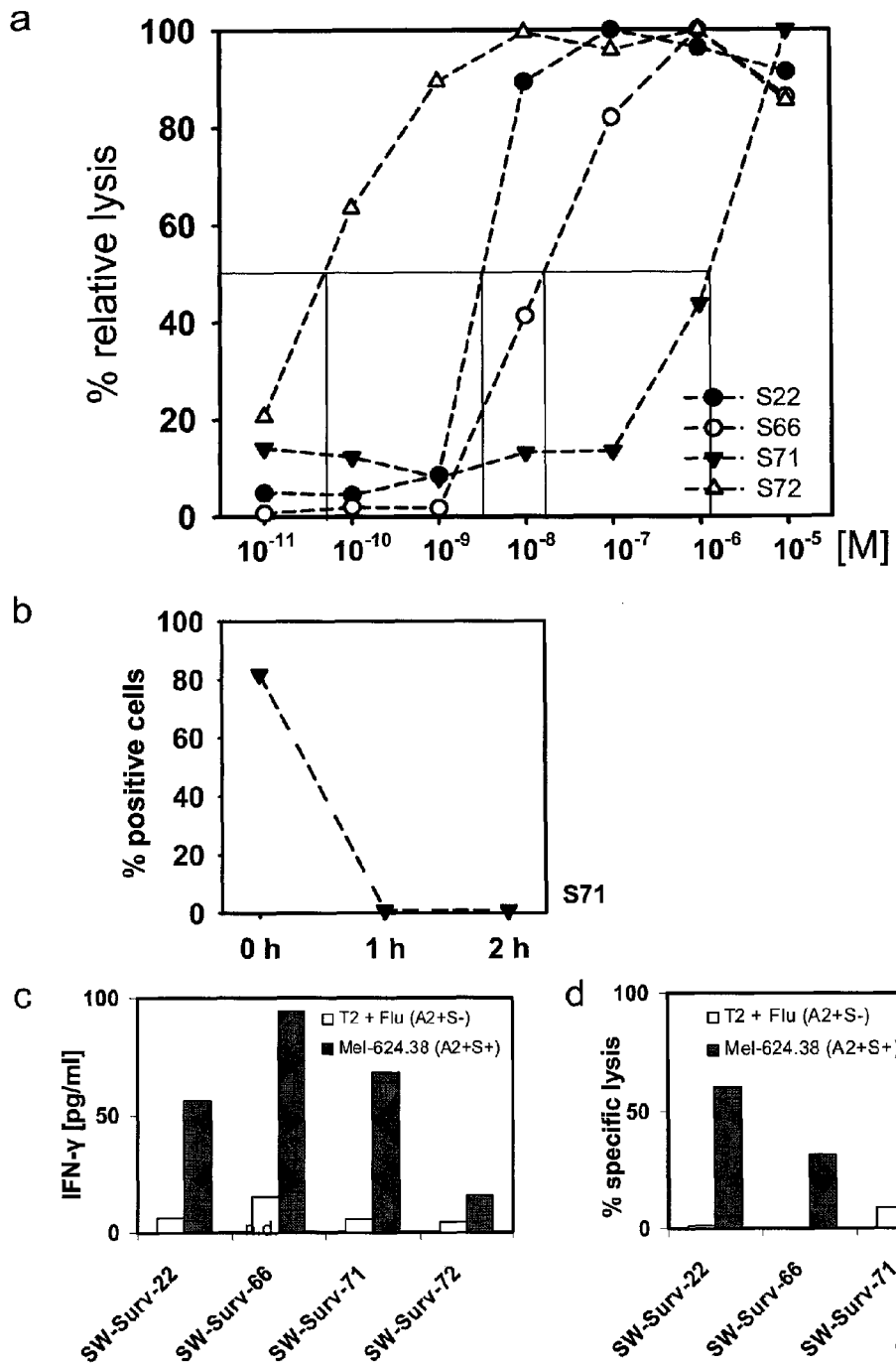
Figure 3: Allo-restricted T cell clones
Specificity: HLA-A2 + survivin-peptide LMLGEFLKL

REPERTOIRE OF ALLO-RESTRICTED PEPTIDE-SPECIFIC T CELL RECEPTOR SEQUENCES AND USE THEREOF

CROSS-REFERENCES TO RELATED APPLICATIONS

The present application is a U.S. National Phase of PCT/EP2010/051565, filed Feb. 9, 2010, which claims the benefit of U.S. Provisional Application Ser. No. 61/150,934, filed on Feb. 9, 2009, the disclosures of which are hereby incorporated herein by reference in their entirety.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 80309-6.TXT, created on Jun. 25, 2013, 57,344 bytes, machine format IBM-PC, MS-Windows operating system, is hereby incorporated by reference in its entirety for all purposes.

FIELD OF THE INVENTION

The present invention is directed to a kit-of-parts or composition containing nucleic acid sequences coding for high-avidity, allo-restricted TCR, wherein the TCR are independently directed against the tyrosinase antigen, the melan-A antigen and the survivin antigen. The invention is further directed to a kit-of-parts or composition containing at least three groups of transgenic lymphocytes transformed with vectors coding for TCR against said antigens. Furthermore, the present invention provides a pharmaceutical composition and its use in the treatment of diseases involving malignant cells expressing said tumor-associated antigens. The invention further relates to a nucleic acid molecule coding for a TCR that recognizes the survivin antigen, a TCR encoded thereby and a T cell expressing said TCR. Further, the invention discloses a vector, a cell and a pharmaceutical composition encoding/containing same and their use in the treatment of diseases involving malignant cells expressing survivin.

BACKGROUND OF THE INVENTION

T cell responses against tumors are often directed against self-MHC molecules presenting peptides derived from over-expressed self-proteins. In general, T cells with high avidity for self-peptide/self-MHC ligands are eliminated by negative selection to prevent autoimmunity. The TCR affinity of remaining T cells specific for self-ligands is normally low, however high-avidity T cells are needed to effectively eradicate tumors. Because negative selection is limited to self-MHC molecules, T cells that recognize allogeneic MHC molecules have not undergone negative selection. Thus, if peptides are presented by allogeneic MHC molecules, it is feasible to obtain high-avidity T cells specific for common tumor-associated ligands derived from over-expressed self-proteins. T cells that recognize allogeneic MHC molecules irrespective of a specific peptide can be distinguished in vitro from allo-restricted peptide-specific T cells at the clonal level and excluded.

Significant tumor regression can occur following adoptive transfer of T cells with anti-tumor specificity. However, patient-derived T cells may have sub-optimal activity. Furthermore, T cells with appropriate specificity and function for effective tumor eradication are often not available for patients with rapidly progressing tumors. Therefore, there is current interest in using pre-characterized TCR genes to create designer lymphocytes for adoptive cell therapies. Expression of TCR-transgenes in activated lymphocytes can imbue recipient lymphocytes with anti-tumor activities comparable to the original T cells (Morris et al. Blood Rev (2006) 20, 61-69; Schumacher et al., Nat. Rev. Immunol. (2002) 2, 512-519). Moreover, some transgenic TCR can displace endogenous TCR sequences, yielding lymphocytes that express monoclonal TCR.

The first clinical trials using adoptive transfer of TCR-transgenic T cells in melanoma patients achieved clinical disease-free status in 2 of 17 patients with rapidly progressing disease (Morgan et al. Science (2006) 314, 126-129). Higher rates of clinical efficacy were obtained in patients receiving TCR transgenic lymphocytes transduced with a TCR of higher affinity but some undesired responses were noted against normal tissues. These results demonstrated the therapeutic potential of this approach however they also revealed the need to evaluate a variety of TCR sequences that recognize the same ligand but have different affinities in order to identify the most suitable TCR sequences for clinical development that can be used to achieve optimal elimination of tumor cells while showing the lowest undesired activity directed against normal, non-malignant tissues.

A number of T cell clones with specificity for various tumor-associated antigens have been reported over the years. Most of these TCR are restricted by self-MHC molecules. Further, available TCR are often of low-avidity. Multiple TCR with good capacity to recognize tumor cells via different tumor-associated antigens (TAA) are often lacking.

In the prior art, several scientific and patent documents are existing which describe TCR that are able to recognise and bind specific antigens, for example tyrosinase. Visseren et al. (Int. J. Cancer (1997) 72, 1122-1128) describe the affinity and specificity of several tyrosinase-specific TCR and suggest to use these TCR as a specific treatment of melanoma patients. Roszkowski et al. (J. Immunol. (2003) 170, 2582-2589 and Cancer Res. (2005) 65, 1570-1576) are likewise characterising tyrosinase-specific TCR.

U.S. Pat. No. 5,906,936 is directed to cytotoxic T-cells which kill non-MHC-restricted target cells independent of MHC-restriction and not to T-cells, which utilize specific TCR sequences that recognize MHC-restricted ligands.

WO97/32603 is directed to a method for producing non-human TCR and TCR specific for human HLA-restricted tumor antigens. Furthermore, the TCR-nucleic acids and recombinant T-cells are described as well as the administration of TCR recombinant T-cells for the treatment of several diseases.

WO2007/065957 describes an effector T-cell transfected with an antigen specific TCR coding RNA wherein the transfected T-cell recognizes the antigen in a complex with the MHC-molecule and binds the same. As potential tumor antigens, MART-1 (melan-A), tyrosinase and survivin are named.

WO2008/039818 discloses MART-1 and tyrosinase-specific TCR sequences and describes the enhancement of antigen recognition by substitution in the CDR2 region.

The above prior art TCR sequences are all derived from autologous or xenogeneic, but not allogeneic, sources.

For example, TCR sequences are from peripheral blood or from tumor-infiltrating lymphocytes of HLA-A2-positive melanoma patients. This means that all these TCR are HLA-A2 self-restricted TCRs, or, are HLA-DP4 self-restricted, NY-ESO-1 specific, both derived from autologous sources.

As an alternative, as disclosed in WO97/32603, the TCR is derived from an HLA-A2 transgenic mouse and, therefore, the sequence is xenogeneic in this case.

However, the available prior art documents do not show TCR sequences, which are allo-restricted and specific for the survivin, tyrosinase and melan A antigens.

Thus, there is still an important need to find means to generate T cells that bear TCR with high functional avidity that have the capacity to recognize specific ligands on tumor cells.

Immune selection of tumor cells poses a severe problem in TCR-based therapies. Tumors tend to be genetically unstable and may lose their antigens by mutation. This instability may lead to the generation of antigen-loss variants which are able to escape the immune response. Therefore, if tumor cells are attacked by T cells recognizing only one single TAA specificity, this might lead to a reduced or even absent success of therapy due to outgrowth of tumor cells lacking expression of the specific TAA.

Therefore, there is a further need existing to provide a clinical approach to effectively minimize immune selection of tumor cells and to provide a broad and specific attack on tumor cells.

SUMMARY OF THE INVENTION

Therefore, it is an object of the present invention to provide a TCR-based approach in order to overcome the drawbacks of the prior art therapies, in particular to effectively minimize immune selection of tumor cells. It is a further object of the invention to provide a repertoire of TCR which can be effectively used in the treatment of diseases involving malignant cells expressing tyrosinase and/or melan-A and/or survivin, preferably melanomas, gliomas, glioblastomas, and/or rare tumors of ectodermal origin, the like to provide mixtures of TCR-transgenic lymphocytes to target tumors via several different MHC-peptide ligands in order to avoid immune selection of tumor cells that lack expression of a specific TAA. It is a further object of the present invention to provide TCR or functional parts thereof, such as CDR3 regions, which show high affinity against the survivin antigen. It is a still further object of the invention to provide pharmaceutical compositions for use in adoptive cell therapy which allow an effective treatment of diseases involving malignant cells expressing survivin.

These objects are solved by the subject-matter of the independent claims. Preferred embodiments are indicated in the dependent claims.

It is a great advantage to administer mixtures of TCR-transgenic specific T cells to patients to target their tumors via several different MHC-peptide ligands in order to avoid immune selection of tumor cells that lack TAA expression if they are attacked by T cells with only a single specificity.

The inventors generated high-avidity, allo-restricted peptide-specific T cells that provide suitable sources of TCR sequences for selection of TCR that can be developed for clinical application. Furthermore, the inventors have generated a series of T cell clones and demonstrated their high-avidity and tumor-specificity for three distinct melanoma-associated antigens. In addition, one of the antigens for which they have generated a repertoire of TCR sequences, namely survivin, is broadly expressed in a variety of tumors and therefore, these sequences can also be used for treatment of tumors other than melanoma.

The use of repertoires of TCR with different specificities does not only provide a broader basis of an attack of tumor cells, helping to avoid immune selection of TAA loss variants, but will also allow patients to be treated if their tumors naturally fail to express any one of the individual TAA that are targeted by the TCR. Thereby, future adoptive T cell therapies can be realized for more patients by employing these TCR sequences to develop "off the shelf" reagents for transduction of patient-derived lymphocytes.

The combination of TCR used in the present invention, i.e. TCR directed against the survivin, tyrosinase and optionally melon A antigen, is particularly effective in vivo in minimizing immune selection of tumor cells and in defeating malignancies. In other words, also in case of immune selection, there is still a high probability that the tumor to be attacked still expresses at least one of the named TAA and thus can be effectively recognized and defeated. This is in contrast to prior art approaches, where tumor cells are attacked by T cells recognizing only one single TAA specificity, potentially leading to a reduced or even absent success of therapy due to outgrowth of tumor cells lacking expression of the specific TAA.

DETAILED DESCRIPTION OF THE INVENTION

According to a first aspect, the invention provides a kit-of-parts or composition comprising:
 a) a group of vectors containing nucleic acid sequences coding for high-avidity, allo-restricted TCR, wherein the TCR are directed against the tyrosinase antigen;
 b) a group of vectors containing nucleic acid sequences coding for high-avidity, allo-restricted TCR, wherein the TCR are directed against the melan-A antigen; and
 c) a group of vectors containing nucleic acid sequences coding for high-avidity, allo-restricted TCR, wherein the TCR are directed against the survivin antigen.

As used herein, the term "kit-of-parts" shall encompass an entity of physically separated components, which are intended for individual use, but in functional relation to each other. This means that the individual parts of the kit are provided for simultaneous or subsequent administration. If all components (or groups) are provided in mixed form, they are defined herein as a "composition" and not as a kit-of-parts.

In an embodiment, the vector used in the kit-of-parts or composition is a plasmid, shuttle vector, phagemide, cosmid, expression vector, retroviral vector, adenoviral vector or particle. In the context of the present invention, a "vector" shall mean a nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known to those of ordinary skill in the art. A vector preferably is an expression vector that includes a nucleic acid according to the present invention operably linked to sequences allowing for the expression of said nucleic acid.

In a preferred embodiment, the kit-of-parts or composition contains the following selection of vectors:

The vectors of group a) are comprising at least one CDR3 sequence according to SEQ ID NO: 1-10, or at least one nucleic acid sequence coding for the amino acid sequence of SEQ ID NO: 29-38 and/or the vectors of group b) are comprising at least one CDR3 sequence according to SEQ ID NO: 11-20 or at least one nucleic acid sequence coding for the amino acid sequence of SEQ ID NO: 39-48, and/or the vectors of group c) are comprising at least one CDR3 sequence according to SEQ ID NO: 21-28 or at least one nucleic acid sequence coding for the amino acid sequence of SEQ ID NO: 49-56.

It is noted that within each group, a ranking of the most promising sequences is existing, being from the most to the less preferred sequence:

Directed against the tyrosinase antigen: CDR3 sequence according to SEQ ID NO: 1, 2, 8, 9, 10, 3, 4, 5, 6, 7 or the nucleic acid sequence coding for the amino acid sequence of SEQ ID NO: 29, 30, 36, 37, 38, 31, 32, 33, 34, 35.

Directed against the melan-A antigen: CDR3 sequence according to SEQ ID NO: 19, 20, 15, 16, 17, 18, 11, 12, 13, 14 or the nucleic acid sequence coding for the amino acid sequence of SEQ ID NO: 47, 48, 43, 44, 45, 46, 39, 40, 41, 42.

Directed against the survivin antigen: CDR3 sequence according to SEQ ID NO: 27, 28, 23, 24, 25, 26, 21, 22 or the nucleic acid sequence coding for the amino acid sequence of SEQ ID NO: 55, 56, 51, 52, 53, 54, 49, 50.

It is further noted that, in the present invention, SEQ ID NO:s defining the alpha and beta chains of a precise TCR are not grouped separately. Although it is contemplated that all alpha chain sequences may be combined with all beta chain sequences (if directed against the same antigen), it is preferred that the alpha and the beta chain sequences derived from the same clone are used in combination. For example, a preferred TCR against the survivin antigen may comprise SEQ ID NO: 27 for the alpha chain sequence and SEQ ID NO: 28 for the beta chain sequence (both derived from the same clone, i.e. SW-Surv-72).

The invention further provides derivatives of said CDR3 sequences wherein the CDR3 region has been altered by one or more additions and/or deletions of an overall number of from 1-5 amino acids, but not more than 1-3 contiguous amino acids and/or conservative substitutions of from 1-6 amino acids and wherein the tumor antigen recognizing characteristics are maintained or improved.

This means, more precisely, that additions or deletions may be performed to an extent that 1-5 amino acids are added or deleted in the CDR3 region. If more than one addition or deletion is performed, the overall number of added or deleted amino acids may not exceed 5 amino acids. Further, one single addition or deletion at one site may only be in the range of 1-3 amino acids, i.e. 1-3 contiguous amino acids, since the ligand binding capacity might be deteriorated by performing larger additions/deletions.

In a further embodiment, the vectors are each comprising a nucleic acid molecule coding for the V(D)J regions of a TCR that recognizes the respective tumor antigen, the vectors comprising a) the nucleic acid sequence of SEQ ID NO: 57, 59, 61, 62, 64, or 65 coding for the α-chain and/or the nucleic acid sequence of SEQ ID NO: 58, 60, 63, or 66 coding for the β-chain of a TCR directed against the tyrosinase antigen, b) the nucleic acid sequence of SEQ ID NO: 67, 69, 71, 73, or 75 coding for the α-chain and/or the nucleic acid sequence of SEQ ID NO: 68, 70, 72, 74, or 76 coding for the β-chain of said TCR directed against the melan-A antigen, and c) the nucleic acid sequence of SEQ ID NO: 77, 79, 81, or 83 coding for the α-chain and/or the nucleic acid sequence of SEQ ID NO: 78, 80, 82, or 84 coding for the β-chain of said TCR directed against the survivin antigen, or a derivative of these sequences, coding for the α- or β-chain, wherein the chain has been altered by one or more additions or deletions of from 1-15 amino acids, the additions or deletions being outside the CDR3 region of each chain and/or by conservative substitutions of from 1-15 amino acids, wherein the tumor antigen recognizing characteristics are maintained or improved.

Also here, a ranking of the most promising sequences is existing, being from the most to the less preferred sequence:

Directed against the tyrosinase antigen: the nucleic acid sequence of SEQ ID NO: 57, 59, 64, 65, 61, 62, coding for the α-chain and/or the nucleic acid sequence of SEQ ID NO: 58, 60, 66, 63 coding for the β-chain of a TCR directed against the tyrosinase antigen.

Directed against the melan-A antigen: the nucleic acid sequence of SEQ ID NO: 75, 71, 73, 67, 69 coding for the α-chain and/or the nucleic acid sequence of SEQ ID NO: 76, 72, 74, 68, 70 coding for the β-chain of said TCR directed against the melan-A antigen.

Directed against the survivin antigen: the nucleic acid sequence of SEQ ID NO: 83, 79, 81, and 77 coding for the α-chain and/or the nucleic acid sequence of SEQ ID NO: 84, 80, 82, and 78 coding for the β-chain of said TCR directed against the survivin antigen, The term "nucleic acid" as used herein refers to a naturally-occurring nucleic acid that is not immediately contiguous with both of the sequences with which it is immediately contiguous (one on the 5' end and one on the 3' end) in the naturally-occurring genome of the cell from which it is derived. For example, a nucleic acid can be, without limitation, a recombinant DNA molecule of any length, provided one of the nucleic acid sequences normally found immediately flanking that recombinant DNA molecule in a naturally-occurring genome is removed or absent. Thus, a nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, or adenovirus). In addition, an isolated nucleic acid can include a recombinant DNA molecule that is part of a hybrid or fusion nucleic acid sequence.

Furthermore, the term "nucleic acid" as used herein also includes artificially produced DNA or RNA sequences, such as those sequences generated by DNA or RNA synthesis based on in silico information.

The invention is also directed to a kit-of-parts or composition comprising TCR, preferably soluble TCR, encoded by the above indicated nucleic acids and directed against the survivin, melan-A and tyrosinase antigens. These TCR may as an alternative be synthetic proteins.

The nucleic acids of the invention can comprise natural nucleotides, modified nucleotides, analogues of nucleotides, or mixtures of the foregoing as long as they are capable of causing the expression of a polypeptide in vitro, and preferably, in a T cell. The nucleic acids of the invention are preferably RNA, and more preferably DNA.

Furthermore, the present invention also comprises derivatives of the above described nucleic acid molecules, wherein, related to the above sequences, the sequence has been altered by additions, deletions and/or substitutions and wherein the tumor antigen recognizing characteristics are maintained or improved.

More precisely, such a derivative is coding for the α- or β-chain, wherein the chain has been altered by one or more additions or deletions of from 1-15 amino acids, the additions or deletions being outside the CDR3 region of each chain, and/or by conservative substitutions of from 1-15 amino acids. It is noted in this connection that also the CDR3 region may be altered, but to a lesser extent. The definition of those amendments is indicated above for the derivatives of fragments coding for the CDR3 region.

Useful changes in the overall nucleic acid sequence in particular are related to codon optimization and the addition of epitope tags, which will be explained in detail below. Such codon optimization can include optimization of expression levels, optimization of avidity for target cells, or both.

In general, it should, however, be noted that the alterations should not diminish or alter the ability of the encoded polypeptide to form part of a TCR that recognizes tumor associated antigens in the context of an MHC molecule, but should facilitate destruction of a tumor cell, and preferably facilitate the regression of a tumor, or other cancerous state.

For example, alterations can be made which lead to conservative substitutions within the expressed amino acid sequence. These variations can be made in complementarity determining and non-complementarity determining regions of the amino acid sequence of the TCR chain that do not affect function. However, as noted above, additions and deletions should not be performed in the CDR3 region (for example an addition of epitope tags).

The concept of "conservative amino acid substitutions" is understood by the skilled artisan, and preferably means that codons encoding positively-charged residues (H, K, and R) are substituted with codons encoding positively-charged residues, codons encoding negatively-charged residues (D and E) are substituted with codons encoding negatively-charged residues, codons encoding neutral polar residues (C, G, N, Q, S, T, and Y) are substituted with codons encoding neutral polar residues, and codons encoding neutral non-polar residues (A, F, I, L, M, P, V, and W) are substituted with codons encoding neutral non-polar residues. These variations can spontaneously occur, be introduced by random mutagenesis, or can be introduced by directed mutagenesis. Those changes can be made without destroying the essential characteristics of these polypeptides, which are to recognize antitumor antigens in the context of an MHC with high avidity so as to enable the destruction of cancer cells. The ordinarily skilled artisan can readily and routinely screen variant amino acids and/or the nucleic acids encoding them to determine if these variations substantially lessen or destroy the ligand binding capacity by methods known in the art.

As outlined above, the TCR nucleic sequences may have been altered in order to provide codon optimization. Codon optimization is a generic technique to achieve optimal expression of a foreign gene in a cell system. Selection of optimum codons depends on codon usage of the host genome and the presence of several desirable and undesirable sequence motifs. It is noted that codon optimization will not lead to an altered amino acid sequence and, thus, will not fall under the definition of a conservative substitution as contained in this application.

In a still further embodiment, the vectors contain nucleic acids coding for functional TCR α and/or β chain fusion proteins, comprising:
a) at least one epitope-tag, and
b) the amino acid sequence of an α and/or β chain of a TCR as defined hereinabove, wherein said epitope-tag is selected from
i) an epitope-tag added to the N- and/or C-terminus of said α and/or β chain, or added into the α and/or β chain sequence, but outside the CDR3 region,
ii) an epitope-tag inserted into a constant region of said α and/or β chain, and
iii) an epitope-tag replacing a number of amino acids in a constant region of said a and/or chain.

Epitope tags are short stretches of amino acids to which a specific antibody can be raised, which in some embodiments allows one to specifically identify and track the tagged protein that has been added to a living organism or to cultured cells. Detection of the tagged molecule can be achieved using a number of different techniques. Examples of such techniques include: immunohistochemistry, immunoprecipitation, flow cytometry, immunofluorescence microscopy, ELISA, immunoblotting ("Western"), and affinity chromatography. Epitope tags add a known epitope (antibody binding site) on the subject protein, to provide binding of a known and often high-affinity antibody, and thereby allowing one to specifically identify and track the tagged protein that has been added to a living organism or to cultured cells.

In the context of the present invention, a "functional" T-cell receptor (TCR) α- and/or β-chain fusion protein shall mean an α- and/or β-chain fusion protein that, although the chain includes the epitope-tag and/or has a tag attached to it, maintains at least substantial fusion protein biological activity in the fusion. In the case of the α- and/or β-chain of a TCR, this shall mean that both chains remain able to form a T-cell receptor (either with a non-modified α- and/or β-chain or with another inventive fusion protein α- and/or β-chain) which exerts its biological function, in particular binding to the specific peptide-MHC complex of said TCR, and/or functional signal transduction upon peptide activation.

Preferred is a functional T-cell receptor (TCR) α- and/or β-chain fusion protein according to the present invention, wherein said epitope-tag has a length of between 6 to 15 amino acids, preferably 9 to 11 amino acids.

Even more preferred is a functional T-cell receptor (TCR) α- and/or β-chain fusion protein according to the present invention, wherein said T-cell receptor (TCR) α- and/or β-chain fusion protein comprises two or more epitope-tags, either spaced apart or directly in tandem. Embodiments of the fusion protein can contain 2, 3, 4, 5 or even more epitope-tags, as long as the fusion protein maintains its biological activity/activities ("functional").

Preferred is a functional T-cell receptor (TCR) α- and/or β-chain fusion protein according to the present invention, wherein said epitope-tag is selected from, but not limited to, CD20 or Her2/neu tags, or other conventional tags such as a myc-tag, FLAG-tag, T7-tag, HA (hemagglutinin)-tag, His-tag, S-tag, GST-tag, or GFP-tag. The myc, T7, GST, GFP tags are epitopes derived from existing molecules. In contrast, FLAG is a synthetic epitope tag designed for high antigenicity (see, e.g., U.S. Pat. Nos. 4,703,004 and 4,851,341). The myc tag can preferably be used because high quality reagents are available to be used for its detection. Epitope tags can of course have one or more additional functions, beyond recognition by an antibody. The sequences of these tags are described in the literature and well known to the person of skill in art.

In the functional T-cell receptor (TCR) α- and/or β-chain fusion protein according to the present invention, said fusion protein may be for example selected from two myc-tag sequences that are attached to the N-terminus of an α-TCR-chain and/or 10 amino acids of a protruding loop region in the β-chain constant domain being exchanged for the sequence of two myc-tags.

In an embodiment of the present invention, the inventors inserted an amino acid sequence that corresponds to a part of the myc protein (myc-tag) at several reasonable sites into the structure of a T cell receptor and transduced this modified receptor into T cells (see examples below). By introducing a tag into the TCR structure, it is possible to deplete the modified cells by administering the tag-specific antibody to the patient.

Those functional TCR fusion proteins may be used in a method for selecting a host cell population expressing a fusion protein selected from the group consisting of a fusion protein comprising a) at least one epitope-providing amino acid sequence (epitope-tag), and b) the amino acid sequence of an α- and/or β-chain of a TCR as defined above, wherein said epitope-tag is selected from an epitope-tag added to the N- and/or C-terminus of said α- and/or β-chain or added into the α- and/or β-chain sequence, but outside the CDR3 region, an epitope-tag inserted into a constant region of said α- and/or β-chain, and an epitope-tag replacing a number of amino acids in a constant region of said α- and/or β-chain; and a TCR comprising at least one fusion protein as above on the surface of the host cell; comprising contacting host cells in a sample with a binding agent that immunologically binds to the epitope-tag, and selection of said host cells based on said binding.

The present invention further provides an immunoglobulin molecule, anticaline, TCR γ/δ chain having a CDR3 region as defined herein (or a derivative thereof) inserted. Therefore, the kit-of-parts or composition may also comprise a repertoire of said molecules, i.e. a group directed against the tyrosinase antigen, a group directed against the melan-A antigen, and a group directed against the survivin antigen.

In a second aspect, the present invention provides a kit-of-parts or composition comprising at least three groups of transgenic lymphocytes,
   a) a group of transgenic lymphocytes transformed with vectors containing nucleic acid sequences coding for high-avidity, allo-restricted TCR, wherein the TCR are directed against the tyrosinase antigen;
   b) a group of transgenic lymphocytes transformed with vectors containing nucleic acid sequences coding for high-avidity, allo-restricted TCR, wherein the TCR are directed against the melan-A antigen; and
   c) a group of transgenic lymphocytes transformed with vectors containing nucleic acid sequences coding for high-avidity, allo-restricted TCR, wherein the TCR are directed against the survivin antigen,
wherein the vectors and the nucleic acid sequences contained therein are defined as above.

The lymphocytes preferably are CD4$^+$ or CD8$^+$ T lymphocytes, or natural killer cells, and, more preferably, are autologous or allogeneic to the patient.

In a further aspect, the present invention is directed to a kit-of-parts or composition as defined above, comprising groups a) and c) of the vectors or of the transgenic lymphocytes. This kit-of-parts or composition according to the invention, thus, is directed against the tyrosinase antigen and the survivin antigen, but not necessarily against the melan-A antigen. The above disclosed principles regarding the kit-of-parts or composition also apply here.

In a still further aspect, the invention is directed to a pharmaceutical composition which comprises the kit-of-parts or composition as defined above and a pharmaceutically acceptable carrier.

The active components of the present invention are preferably used in such a pharmaceutical composition in doses mixed with an acceptable carrier or carrier material, that the disease can be treated or at least alleviated. Such a composition can (in addition to the active component and the carrier) include filling material, salts, buffer, stabilizers, solubilizers and other materials, which are known state of the art.

The term "pharmaceutically acceptable" defines a non-toxic material, which does not interfere with effectiveness of the biological activity of the active component. The choice of the carrier is dependent on the application.

The pharmaceutical composition can contain additional components which enhance the activity of the active component or which supplement the treatment. Such additional components and/or factors can be part of the pharmaceutical composition to achieve synergistic effects or to minimize adverse or unwanted effects.

Techniques for the formulation or preparation and application/medication of active components of the present invention are published in "Remington's Pharmaceutical Sciences", Mack Publishing Co., Easton, Pa., latest edition. An appropriate application is a parenteral application, for example intramuscular, subcutaneous, intramedular injections as well as intrathecal, direct intraventricular, intravenous, intranodal, intraperitoneal or intratumoral injections. The intravenous injection is the preferred treatment of a patient.

According to a preferred embodiment, the pharmaceutical composition is an infusion or an injection.

An injectable composition is a pharmaceutically acceptable fluid composition comprising at least one active ingredient, e.g., an expanded T-cell population (for example autologous or allogenic to the patient to be treated) expressing a TCR. The active ingredient is usually dissolved or suspended in a physiologically acceptable carrier, and the composition can additionally comprise minor amounts of one or more non-toxic auxiliary substances, such as emulsifying agents, preservatives, and pH buffering agents and the like. Such injectable compositions that are useful for use with the fusion proteins of this disclosure are conventional; appropriate formulations are well known to those of ordinary skill in the art.

In another aspect, the present invention is directed to a method of treating a patient in need of adoptive cell therapy, said method comprising administering to said patient a pharmaceutical composition as defined above to said patient. The patient to be treated preferably belongs to the group of HLA-A2-positive patients.

Preferably, said patient suffers from a disease involving malignant cells expressing tyrosinase and/or melan-A and/or survivin antigens, preferably melanomas, gliomas, glioblastomas, and/or rare tumors of ectodermal origin.

In another aspect, kit-of-parts or composition are used for the manufacture of a medicament for use in adoptive cell therapy.

According to a further aspect, the present invention discloses a nucleic acid molecule coding for the V(D)J regions of a TCR that recognizes the survivin antigen and comprising the nucleic acid sequence of SEQ ID NO: 77, 79, 81, or 83 coding for the α-chain and/or the nucleic acid sequence of SEQ ID NO: 78, 80, 82, or 84 coding for the β-chain of said TCR, or a derivative thereof, coding for the α- or β-chain, wherein the chain has been altered by one or more additions or deletions of from 1-15 amino acids, the additions or deletions being outside the CDR3 region of each chain and/or by conservative substitutions of from 1-15 amino acids, wherein the survivin antigen recognizing characteristics are maintained or improved,
or
a fragment thereof coding for a CDR3 region of a TCR recognizing the survivin antigen and having the nucleic acid sequence of SEQ ID NO: 21-28 or coding for the amino acid sequences of SEQ ID NO: 49-56, or a derivative of said fragment, wherein the CDR3 region has been altered by one or more additions and/or deletions of an overall number of from 1-5 amino acids, but not more than 1-3 contiguous amino acids and/or conservative substitutions of from 1-6 amino acids and wherein the survivin antigen recognizing characteristics are maintained or improved.

Also here, a ranking of the most promising sequences is existing, being from the most to the less preferred sequence: the nucleic acid sequence of SEQ ID NO: 83, 79, 81, and 77 coding for the α-chain and/or the nucleic acid sequence of SEQ ID NO: 84, 80, 82, and 78 coding for the β-chain of said TCR directed against the survivin antigen, For the CDR3 region of a TCR recognizing the survivin antigen, the ranking of the nucleic acid sequence is: SEQ ID NO: 27, 28, 23, 24, 25, 26, 21, 22 or the amino acid sequences of SEQ ID NO: 55, 56, 51, 52, 53, 54, 49, 50.

The above remarks regarding fragments or derivatives (variants) do also apply here.

In a further aspect, the invention provides a TCR, preferably a soluble TCR, encoded by a nucleic acid as defined above or comprising one or more the amino acid sequences of SEQ ID NO: 49-56. This preferably also encompasses a functional TCR α and/or β chain fusion protein, comprising:

a) at least one epitope-tag, and
b) the amino acid sequence of an α and/or β chain of a TCR against the survivin antigen as defined above, wherein said epitope-tag is selected from i) an epitope-tag added to the N- and/or C-terminus of said α and/or β chain, or added into the α and/or β chain sequence, but outside the CDR3 region, ii) an epitope-tag inserted into a constant region of said a and/or chain, and iii) an epitope-tag replacing a number of amino acids in a constant region of said α and/or β chain.

The preferred ranking is: SEQ ID NO: 55, 56, 51, 52, 53, 54, 49, 50.

Further provided is a T cell expressing a TCR as above directed against the survivin antigen, or a TCR comprising one of the CDR3 regions as defined above or an immunoglobulin molecule, anticaline, TCR γ/δ chain having a CDR3 region as above inserted.

Furthermore, the invention provides for a vector, preferably a plasmid, shuttle vector, phagemide, cosmid, expression vector, retroviral vector, adenoviral vector or particle and/or vector to be used in gene therapy, which comprises one or more of the nucleic acids as defined above.

In a still further aspect, the invention is directed to a cell, preferably a PBL which has been transformed with the above vector. The step of cloning the T cell receptor (TCR) of the isolated T cells and/or expressing the TCR transgenes in PBMC can be done according to established methods such as those described in Sommermeyer et al., Eur. J. Immunol. (2006) 36, 3052-3059.

In addition, a pharmaceutical composition is provided which comprises a TCR, a T cell, an immunoglobulin molecule, anticaline, TCR γ/δ chain as above and a pharmaceutically acceptable carrier. For further information, see above.

The pharmaceutical composition preferably is used for the manufacture of a medicament for use in adoptive cell therapy, preferably for treating a disease in patients, the disease involving malignant cells expressing the survivin antigen.

Survivin is known to be expressed across most carcinoma cell types and at the same time is absent in normal non-malignant cells.

Therefore, the pharmaceutical composition may be used in the treatment of nearly all conceivable carcinomas.

The present invention now will be illustrated by the enclosed Figures and the Examples. The following examples further illustrate the invention but, of course, should not be construed as limiting its scope.

DESCRIPTION OF THE FIGURES

FIG 1 shows the results of these evaluations for four HLA-A*0201-allo-restricted T cell clones specific for the tyrosinase peptide YMDGTMSQV (SEQ ID NO:85): T cell avidity (FIG. 1a); multimer off-rate (FIG. 1b); IFN-γ secretion assay (FIG. 1c) and cytotoxic killing of melanoma cells (FIG. 1d).

FIG. 2 shows the results of these evaluations for five HLA-A*0201-allo-restricted T cell clones specific for the melan-A peptide ELAGIGILTV (SEQ ID NO:86): T cell avidity (FIG. 2a); multimer off-rate (FIG. 2b); IFN-γ secretion assay (FIG. 2c) and cytotoxic killing of melanoma cells (FIG. 2d).

FIG 3 shows the results of these evaluations for four HLA-A*0201-allo-restricted T cell clones specific for the survivin peptide LMLGEFLKL (SEQ ID NO:87): T cell avidity (FIG. 3a); multimer off-rate (FIG. 3b); IFN-γ secretion assay (FIG. 3c) and cytotoxic killing of melanoma cells (FIG. 3d).

EXAMPLES

To isolate high-avidity T cells bearing TCR that recognize peptides presented by allogeneic major histocompatibility complex (MHC) molecules (i.e. allo-restricted T cells) and efficiently kill tumor cells with corresponding ligands, autologous dendritic cells (DC) obtained from HLA-A*0201-negative healthy donors were used for T cell priming following co-transfection with RNA encoding allogeneic HLA-A*0201 molecules and RNA encoding a selected TAA. Tyrosinase, melan-A and survivin were selected as the TAA; these are self-proteins that are often over-expressed in melanomas, and in the case of survivin many other types of tumors, and serve as examples of common tumor-associated antigens (TAA). DC were used to prime purified, autologous CD8+ T cells using two rounds of stimulation with freshly prepared RNA-pulsed DC. Prior to activation and after stimulation, the frequency of CD8+ T cells with TCR recognizing HLA-A2-peptide complexes was measured using HLA-multimers. Double-positive T cells were assessed after DC stimulation in the established cultures and CD8+ multimer+ cells were isolated by fluorescence-activated cell sorting (Wolff et al. Cytometry A (2004) 57, 120-130. Sorted cells were cloned in limiting dilution cultures and expanded in vitro using antigen-independent stimulation.

The isolated T cell clones were tested for function and specificity and their TCR sequences were determined. Multiple T cell clones showing the required tumor specificity, good T cell avidity, and various TCR multimer off-rates, were identified and the cDNAs encoding their TCR sequences were isolated by RT-PCR and the sequences of the TCR alpha and beta chains were determined (Tables 1-3).

These selected TCR sequences can be expressed in various gene vectors (e.g. retroviral vectors or lentiviral vectors, perhaps even as RNAs for transient expression) in order to allow them to be introduced into recipient lymphocytes. The primary sequences can be changed by codon optimization and other genetic modifications to improve TCR protein expression and alpha and beta chain pairing to provide better TCR expression in recipient lymphocytes.

Four assays were used to demonstrate the tumor-associated specificity of the T cell clones that serve as the sources of TCR sequences for the three different melanoma-associated antigens:

Functional T cell avidity for MHC-peptide ligand recognition was measured in a $^{51}$Cr-release assay using HLA-A2$^+$ T2 cells pulsed with graded amounts of exogenous peptide as target cells. The peptide concentration needed for 50% relative lysis defined the value of half-maximum lysis. This assay also confirmed that the T cell clones recognized the specific peptide used for their multimer selection.

HLA-multimer off-rate was used to assess structural TCR-MHC/peptide binding affinity. A slower off-rate indicates that TCR-ligand interactions are more stable and of higher structural affinity.

Interferon-gamma (IFN-γ) secretion assays were used to evaluate function and specificity. The clones were co-cultured with cell lines that express HLA-A2 molecules but differ with respect to expression of the TAAs. The desired specificity was demonstrated when the T cell clones secreted IFN-γ after co-culture with tumor cells expressing both HLA-A2 and the TAA protein but released only background levels of cytokine when co-cultured with HLA-A2 positive cells lacking TAA protein expression.

A standard $^{51}$Cr-release assay was used to assess the capacity of the TCR to activate T cell killing after stimulation with MHC-peptide ligand expressed by melanoma tumor cells. Control tumor cell lines expressing HLA-A2 but not expressing the corresponding TAA were used as negative controls.

The results indicated in the Figures show that for each TAA the selected T cell clones recognize T2 cells pulsed with the appropriate peptide and they show a range of half-maximum responses, indicating that they vary with respect to functional T cell avidity. The clones also vary with respect to multimer off-rates with some showing loss of multimer binding at 1 h and others retaining multimer binding at 2 h. These differences indicate that the TCR of individual clones interact differently with the MHC-peptide ligands and thereby vary in their structural binding affinity.

In all cases, the clones showed functional recognition via IFN-γ secretion and tumor cell killing of target cells expressing the MHC-peptide ligands used respectively for their multimer sorting. These responses were specific since tumor cells failing to express the appropriate TAA were unable to activate either function in the different T cell clones.

Materials and Methods
Cell Lines

The human melanoma cell lines, Mel-A375 (HLA-A2$^+$, tyrosinase$^-$, melan-A$^-$; CRL-1619, American Type Culture Collection (ATCC), Bethesda, Md.), Mel-93.04A12 (HLA-A2$^+$, tyrosinase$^+$, melan-A$^+$; gift of P. Schrier, Department of Immunohematology, Leiden University Hospital, The Netherlands), Mel-624.38 (HLA-A2$^+$, tyrosinase$^+$, survivin$^+$, gift of M. C. Panelli, National Institutes of Health, Bethesda, Md.) as well as the lymphoid cell line T2 (CRL-1992, ATCC) were cultured in RPMI 1640 medium supplemented with 12% fetal bovine serum (FBS), 2 mM L-glutamine and 1 mM sodium-pyruvate and non-essential amino acids.

Production of Tyrosinase, Melan-A, Survivin and HLA-A2 ivt-RNA

The plasmid pCDM8-HLA-A2 with HLA-A*0201 cDNA, pZeoSV2+/huTyr with tyrosinase cDNA, pcDNAI/Amp/Aa1 with melan-A cDNA and the pGEM4Z/survivin/A64 plasmid were linearized and used as in vitro transcription templates to produce RNA with the aid of the mMESSAGE mMACHINE T7 kit (Ambion, Austin, Tex.) according to the manufacturer's instructions.

De Novo Priming of T Cells with RNA-Pulsed DC

Blood samples from healthy donors were collected after informed consent and with approval of the Institutional Review Board of the University Hospital of the Ludwig-Maximilians-University, Munich, Germany. Peripheral blood lymphocytes (PBL) were isolated by Ficoll density gradient centrifugation. PBL were resuspended in 15 ml very low endotoxin (VLE) RPMI 1640 medium (Biochrom, Berlin, Germany) supplemented with 1.5% human serum (DC medium) at $7.5 \times 10^6$ cells per 75 cm$^2$ culture flask and incubated at 37° C. and 5% CO$_2$ for 1 h. Non-adherent cells were carefully removed by washing. Mature DC were prepared from adherent monocytes and transfected with ivt RNA via electroporation as previously described (Javorovic et al. J. Immunother (2008) 31, 52-62.) DC of HLA-A2$^+$ donors were loaded with 24 μg tyrosinase, melan-A or survivin ivt-RNA and DC of HLA-A$^-$ donors were co-transfected with 24 μg of the individual TAA-encoding RNA and 48 μg HLA-A2 ivt-RNA. On the same day, autologous T lymphocytes were enriched from PBL via negative selection using a commercial kit according to the manufacturer's instructions (CD8$^+$ T cell Isolation Kit II (human), Miltenyi, Bergisch Gladbach, Germany). Co-cultures were initiated 10 h after DC electroporation in 24-well plates (TPP, Trasadingen, Switzerland) by adding $1 \times 10^5$ RNA-pulsed DC to $1 \times 10^6$ CD8$^+$ T cells in RPMI 1640, supplemented with 10% heat-inactivated human serum, 4 mM L-glutamine, 12.5 mM HEPES, 50 μM β-mercaptoethanol and 100 U/ml penicillin/streptomycin (T cell medium). IL-7 (5 ng/ml) (Promokine, Heidelberg, Germany) was added on day 0 and 50 U/ml IL-2 (Chiron Behring, Marburg, Germany) was added after 2 days and then on every 3$^{rd}$ subsequent day. Addition of IL-2 was delayed to decrease proliferation of non-specific CD8$^+$ T cells. The 2$^{nd}$ stimulation of primed T cells was made after seven days using freshly prepared RNA-pulsed DC.

HLA-Multimer Staining and Sorting

Prior to stimulation and six days after the 2$^{nd}$ stimulation of CD8-enriched T cells with RNA-pulsed DC, HLA-A2-restricted tyrosinase-specific T cells were detected by staining with a PE-labeled HLA-A*0201/htyr$_{369-377}$ peptide/human β$_2$m multimer, anti-CD8-APC antibody (clone RPA-T8, BD Pharmingen, Franklin Lakes, N.J.) and propidium iodide (PI: 2 μg/ml). Up to $1 \times 10^6$ of cells were incubated in 50 μl volume for 25 min with 4 μg PE-labeled multimer on ice in the dark. For sorting, up to $5 \times 10^6$ cells were incubated with 12 μg multimer in 100 μl PBS+0.5% human serum. CD8-APC antibody was then added at 1/50 for an additional 25 min. After staining cells were washed twice and either fixed in FACS buffer with 1% paraformaldehyde and analysed by flow cytometry using a FACSCalibur (BD Biosciences) or diluted in PBS+0.5% human serum with PI for sorting. $20-50 \times 10^6$ total cells per priming culture were stained for sorting. PI-negative cells were gated and CD8$^+$multimer$^+$ T cells were sorted on a FACSAria cell sorter (BD Biosciences) with a 70 μm nozzle, at a rate of 15,000 events/s. A PE-labeled HLA-A*0201/hmel.A$_{27-35}$ peptide/human β$_2$m multimer was used for isolation of HLA-A2-restricted melan-A-specific T cells and an R-PE-labeled Pro5® MHC pentamer, HLA-A*0201/hsurvivin$_{96-104}$ peptide (Proimmune, Oxford, United Kingdom), was used for sorting of HLA-A2-restricted survivin-specific T cells. Pentamer staining was performed according to the manufacturer's instructions.

For HLA-multimer off-rate assays, cells were washed after multimer binding and resuspended in FACS buffer containing saturating amounts of BB7.2 monoclonal antibody to capture detached multimers and prevent rebinding to T cells. After 1 or 2 h, samples were fixed and analysed by flow cytometry.

Culture of Peptide-Specific T Cell Clones

Multimer-sorted T cells were cloned by limiting dilution. Clones were plated in 96-well round-bottom plates (TPP) in 200 µl/well T cell medium. 50 IU/ml IL-2 was supplemented every 3 days with 5 ng/ml IL-7 and 10 ng/ml IL-15 (Pepro-Tech Inc., Rocky Hill, N.J.) every 7 days. T cell clones were stimulated non-specifically with anti-CD3 antibody (0.1 µg/ml; OKT-3) and provided with $1 \times 10^5$ feeder cells per 96-well, consisting of irradiated (50 Gy) PBL derived from a pool of five unrelated donors and $1 \times 10^4$ irradiated (150 Gy) EBV-transformed allogeneic B-LCL every two weeks. Proliferating T cells were transferred into 24-well plates (TPP) and cultured in 1.5 ml T cell medium plus cytokines. $1 \times 10^6$ allogeneic irradiated PBL and $1 \times 10^5$ irradiated EBV-transformed allogeneic B-LCL were added per well as feeder cells in 24-well plates. Clonality was determined by TCR β-chain sequence determination.

Peptide Loading of T2 Cells

For exogenous peptide pulsing, $1 \times 10^6$ T2 cells were incubated at 37° C. and 5% $CO_2$ for 2 h with 10 µg/ml human β2-microglobulin (Calbiochem, San Diego, Calif.) and titrating amounts, ranging from $10^{-5}$ M to $10^{-11}$ M, of the following peptides: tyrosinase peptide YMD (tyrosinase$_{369-377}$ YMDGTMSQV (SEQ ID NO:85), Metabion, Martinsried, Germany), melan-A peptide ELA (melan-A$_{27-35}$ ELAGIGILTV (SEQ ID NO:86), Metabion) and survivin peptide LML (survivin$_{96-104}$ LMLGEFLKL (SEQ ID NO:87), Metabion). T2 cells pulsed with $10^{-5}$ M of influenza peptide GIL (influenza matrix protein$_{58-66}$ GILGFVTL (SEQ ID NO:88), Metabion) served as control. After washing, peptide-loaded T2 cells were used as target cells in cytotoxicity assays.

IFN-γ Release Assay

For investigation of specificity, T cell clones ($2 \times 10^3$ cells in 100 µl) were incubated with the respective melanoma cell lines ($1 \times 10^4$ cells in 100 µl). Culture supernatants were harvested after 24 h co-culture and assessed by a standard ELISA using the OptEIA™ Human IFN-γ Set (BD Biosciences Pharmingen). Data represent mean values.

Cytotoxicity Assay

Cytotoxic activity of T cell clones was analysed in a standard 4 h 51-chromium release assay. Melanoma cell lines and peptide-loaded T2 cells were used as target cells. Briefly, $1 \times 10^6$ target cells were labelled with 100 µCi $Na_2{}^{51}CrO_4$ (ICN Biochemicals, Irvine, Calif.) for 1-1.5 h. $^{51}$Cr-labelled target cells were cultured with T cells in 100 µl/well RPMI 1640 with 12% FCS in V-bottom 96-well tissue culture plates (Greiner, Solingen, Germany). T cells were serially diluted and co-cultured with $1 \times 10^3$ melanoma target cells/well to provide graded effector cell to target cell (E:T) ratios from 2.5:1 to 10:1. For determination of functional avidity, $1 \times 10^4$ T cells were added to $1 \times 10^3$ peptide-pulsed T2 cells loaded with titrated amounts of peptide, giving a constant E:T of 10:1.

After 4 h co-culture at 37° C., 50 µA of supernatant were collected and radioactivity was measured in a gamma counter. The percentage of specific lysis was calculated as: 100×(experimental release−spontaneous release)/(maximum release−spontaneous release). Spontaneous release was assessed by incubating target cells in the absence of effector cells and was generally less than 15%. For the calculation of percent relative lysis, the maximum percent specific lysis was set to the reference value of 100% and corresponding values were calculated corresponding to this reference. To determine half-maximum lysis, percent relative lysis was plotted against peptide concentration. The peptide concentration at which the curve crossed 50% relative lysis was taken as the value of half-maximum lysis.

TCR Analysis

For the T-cell receptor analysis of the tyrosinase-, melan-A- and survivin-specific clones, part of the TCR alpha-chains and beta-chains containing the CDR3 region was amplified by RT-PCR using a panel of TCR Vα and TCR Vβ primers combined with a respective TCR constant region primer. Products were sequenced and assigned according to IMGT (Table 1-3; IMGT, the international ImMunoGeneTics information System®, http://imgt.cines.fr).

TABLE 1

TCR-CDR3 sequences of tyrosinase-specific allorestricted T cell clones

| | |
|---|---|
| tyrosinase-specific | T58 alpha-chain: TRAV1-2 AJ28<br>TGTGCTGTGACATACTCTGGGGCTGGGAGTTACCAACTC (SEQ ID NO: 1)<br>C A V T Y S G A G S Y Q L (SEQ ID NO: 29)<br>T58 beta chain: TRBV13 BD1 BJ1-4<br>TGTGCCAGCAGTCAGAAACAGGGCTGGGAAAAACTG (SEQ ID NO: 2)<br>C A S S Q K Q G W E K L (SEQ ID NO: 30) |
| tyrosinase-specific | T43 alpha-chain: TRAV3 AJ28<br>TGTGCTGTGAGAGACCCTGGGGCTGGGAGTTACCAACTC (SEQ ID NO: 3)<br>C A V R D P G A G S Y Q L (SEQ ID NO: 31)<br>T43 beta-chain: TRBV11-3 BD2 BJ2-1<br>TGTGCCAGCAGCTTAGAACGGGAGGGAACCAATGAGCAG (SEQ ID NO: 4)<br>C A S S L E R E G T N E Q (SEQ ID NO: 32) |
| tyrosinase-specific | Di111 alpha-chain 1: TRAV8-2 AJ20<br>TGTGTTGTGAGTTCTAACGACTACAAGCTC (SEQ ID NO: 5)<br>C V V S S N D Y K L (SEQ ID NO: 33)<br>Di111 alpha-chain 2: TRAV3 AJ28<br>TGTGCTGTGAGAGACCCTGGGGCTGGGAGTTACCAACTCACT (SEQ ID NO: 6)<br>C A V R D P G A G S Y Q L T (SEQ ID NO: 34)<br>Di111 beta-chain: TRBV18 BD2 BJ2-7<br>TGTGCCAGCTCACCTTCCGAGGGGTACTCCTACGAGCAG (SEQ ID NO: 7)<br>C A S S P S E G Y S Y E Q (SEQ ID NO: 35) |

TABLE 1-continued

TCR-CDR3 sequences of tyrosinase-specific allorestricted T cell clones

| | |
|---|---|
| tyrosinase-specific | B12 alpha-chain 1: TRAV1-2 AJ38<br>TGTGCTGTGAGACCCGTTAATGCTGGCAACAACCGTAAGCTG (SEQ ID NO: 8)<br>C A V R P V N A G N N R K L (SEQ ID NO: 36)<br>B12 alpha-chain 2: TRAV38-1 AJ28<br>TGTGCTTTCATTAACTCTGGGGCTGGGAGTTACCAACTC (SEQ ID NO: 9)<br>C A F I N S G A G S Y Q L (SEQ ID NO: 37)<br>B12 beta-chain: TRBV7-9 BD2 BJ2-3<br>TGTGCCAGCAGCTCCATTAGCTTACCTAGCACAGATACGCAG (SEQ ID NO: 10)<br>C A S S S I S L P S T D T Q (SEQ ID NO: 38) |

TCR alpha-chain (VJ region), TCR beta-chain (VDJ region) and CDR3 lenghts are designated according to IMGT (IMGT, the international ImMunoGeneTics information system ®, http://imgt.cines.fr)

TABLE 2

TCR-CDR3 sequences of melan-A-specific allorestricted T cell clones

| | |
|---|---|
| melan-A-specific | SW-M1-9 alpha-chain: TRAV12-2 AJ 40<br>TGTGCCGTGACCGGAACCTACAAATAC (SEQ ID NO: 11)<br>C A V T G T Y K Y (SEQ ID NO: 39)<br>SW-M1-9 beta-chain: TRBV3-1 BD2 BJ2-7<br>TGTGCCAGCAGCCCCCTGGGACTAGCGGAGGTTTCCGAGCAG (SEQ ID NO: 12)<br>C A S S P L G L A E V S E Q (SEQ ID NO: 40) |
| melan-A-specific | SW-M1-29 alpha-chain: TRAV30 AJ31<br>TGCGGAGGTAACAATGCCAGACTC (SEQ ID NO: 13)<br>C G G N N A R L (SEQ ID NO: 41)<br>SW-M1-29 beta-chain: TRBV27 BD1 BJ2-2<br>TGTGCCAGCAGGCCCGGGACAGGAATTTTTGACGGGGAGCTG (SEQ ID NO: 14)<br>C A S R P G T G I F D G E L (SEQ ID NO: 42) |
| melan-A-specific | SW-M1-54 alpha-chain: TRAV12-2 AJ31<br>TGTGCCCCAAACAATGCCAGACTC (SEQ ID NO: 15)<br>C A P N N A R L (SEQ ID NO: 43)<br>SW-M1-54 beta-chain: TRBV12-3 BD2 BJ2-2<br>TGTGCCAGCAGCCCCACGATCCTGGTGGAGGCGTACACCGGGGAGCTG (SEQ ID NO: 16)<br>C A S S P T I L V E A Y T G E L (SEQ ID NO: 44) |
| melan-A-specific | SW-M1-66 alpha-chain: TRAV12-2 AJ30<br>TGTGCCGTCGGGGGTGACAAGATC (SEQ ID NO: 17)<br>C A V G G D K I (SEQ ID NO: 45)<br>SW-M1-66 beta-chain: TRBV12-3 BD1 BJ1-5<br>TGTGCCAGCAGTTTGGGACAGGGCTGGCCCCAG (SEQ ID NO: 18)<br>C A S S L G Q G W P Q (SEQ ID NO: 46) |
| melan-A-specific | SW-M1-67 alpha-chain: TRAV12-2 AJ29<br>TGTGCCGTGAGGACACCTCTT (SEQ ID NO: 19)<br>C A V R T P L (SEQ ID NO: 47)<br>SW-M1-67 beta-chain: TRBV30 BD2 BJ2-1<br>TGTGCCTGGAGTTCAAGCGGTTTGGGCGTTGAGCAG (SEQ ID NO: 20)<br>C A W S S S G L G V E Q (SEQ ID NO: 48) |

TCR alpha-chain (VJ region), TCR beta-chain (VDJ region) and CDR3 lenghts are designated according to IMGT (IMGT, the international ImMunoGeneTics information system ®, http://imgt.cines.fr)

TABLE 3

TCR-CDR3 sequences of survivin-specific allorestricted T cell clones

| | |
|---|---|
| survivin-specific | SW-Surv-22 alpha-chain: TRAV20 AJ41<br>TGTGCTGTGCAGGCTTACTCAAATTCCGGGTATGCACTC (SEQ ID NO: 21)<br>C A V Q A Y S N S G Y A L (SEQ ID NO: 49)<br>SW-Surv-22 beta-chain: TRBV29-1 BD1 BJ1-2<br>TGCAGCGTTGAAGACAGCTATGGCTAC (SEQ ID NO: 22)<br>C S V E D S Y G Y (SEQ ID NO: 50) |
| survivin-specific | SW-Surv-66 alpha-chain: TRAV13-1 AJ39<br>TGTGCAGCAAGGGCAGGCAACATGCTC (SEQ ID NO: 23)<br>C A A R A G N M L (SEQ ID NO: 51)<br>SW-Surv-66 beta-chain: TRBV30 BD2 BJ2-7<br>TGTGCCTGGGGTACGGGACTAGCGCTTTACGAGCAG (SEQ ID NO: 24)<br>C A W G T G L A L Y E Q (SEQ ID NO: 52) |
| survivin-specific | SW-Surv-71 alpha-chain: TRAV12-2 AJ31<br>TGTGCCGTGAACAATGCCAGACTC (SEQ ID NO: 25) |

TABLE 3-continued

TCR-CDR3 sequences of survivin-specific allorestricted T cell clones

| | |
|---|---|
| | C A V N N A R L (SEQ ID NO: 53)<br>SW-Surv-71 beta-chain: TRBV30 BD2 BJ2-1<br>TGTGCCTGGAGCATAGGCGCTGAGCAGTTC (SEQ ID NO: 26)<br>C A W S I G A E Q F (SEQ ID NO: 54) |
| survivin-specific | SW-Surv-72 alpha-chain: TRAV14 AJ4<br>TGTGCAATGAGAGAGGGCGGGGGCTACAATAAGCTG (SEQ ID NO: 27)<br>C A M R E G G G Y N K L (SEQ ID NO: 55)<br>SW-Surv-72 beta-chain: TRBV30 BD1 BJ1-1<br>TGTGCCGGACAGGATTTGAACACTGAAGCT (SEQ ID NO: 28)<br>C A G Q D L N T E A (SEQ ID NO: 56) |

TCR alpha-chain (VJ region), TCR beta-chain (VDJ region) and CDR3 lenghts are designated according to IMGT (IMGT, the international ImMunoGeneTics information system ®, http://imgt.cines.fr)

REFERENCES

Morris, E., et al. Generation of tumor-specific T-cell therapies. *Blood Rev* 20, 61-69 (2006).

Schumacher, T. N. T-cell-receptor gene therapy. *Nat Rev Immunol* 2, 512-519 (2002).

Sommermeyer, D., et al. Designer T cells by T cell receptor replacement. *Eur J Immunol* 36, 3052-3059 (2006).

Morgan, R. A., et al. Cancer regression in patients after transfer of genetically engineered lymphocytes. *Science* 314, 126-129 (2006).

Wolff, M., et al. Quantitation of MHC tetramer-positive cells from whole blood: evaluation of a single-platform, six-parameter flow cytometric method. *Cytometry A* 57, 120-130 (2004).

Javorovic, M., et al. Inhibitory effect of RNA pool complexity on stimulatory capacity of RNA-pulsed dendritic cells. *J Immunother* 31, 52-62 (2008).

The invention claimed is:

1. A nucleic acid comprising the nucleotide sequence of SEQ ID NO: 79.

2. A fusion protein, comprising:
   a) at least one epitope-tag, and
   b) an α chain of a TCR encoded by the nucleotide sequence of SEQ ID NO:79,
   wherein said epitope-tag is selected from the group consisting of:
   i) an epitope-tag added to the N- and/or C-terminus of said α chain, or added into the α chain sequence, but outside the CDR3 region,
   ii) an epitope-tag inserted into a constant region of said α chain, and
   iii) an epitope-tag replacing a number of amino acids in a constant region of said α chain.

3. The nucleic acid of claim 1, further comprising a second nucleotide sequence, wherein the second nucleotide sequence is SEQ ID NO:80.

4. The fusion protein of claim 2, wherein said epitope-tag is added to the N- and/or C-terminus of said α chain.

5. The fusion protein of claim 2, further comprising a β chain of a TCR encoded by the nucleotide sequence of SEQ ID NO:80.

6. The fusion protein of claim 5, wherein said fusion protein further comprises at least one epitope-tag selected from the group consisting of:
   i) an epitope-tag added to the N- and/or C-terminus of said β chain, or added into the β chain sequence, but outside the CDR3 region,
   ii) an epitope-tag inserted into a constant region of said β chain, and
   iii) an epitope-tag replacing a number of amino acids in a constant region of said β chain.

7. The fusion protein of claim 6, wherein said epitope-tag is added to the N- and/or C-terminus of said β chain.

8. A vector comprising the nucleic acid of claim 1.

9. A vector comprising the nucleic acid of claim 3.

10. A cell that has been transformed with the vector of claim 8.

11. A cell that has been transformed with the vector of claim 9.

12. A composition comprising a fusion protein and a pharmaceutically acceptable carrier, the fusion protein comprising:
   a) at least one epitope-tag, and
   b) an α chain of a TCR encoded by the nucleotide sequence of SEQ ID NO:79,
   wherein said epitope-tag is selected from the group consisting of:
   i) an epitope-tag added to the N- and/or C-terminus of said α chain, or added into the α chain sequence, but outside the CDR3 region,
   ii) an epitope-tag inserted into a constant region of said α chain, and
   iii) an epitope-tag replacing a number of amino acids in a constant region of said α chain.

13. The composition of claim 12, wherein the fusion protein further comprises a β chain of a TCR encoded by the nucleotide sequence of SEQ ID NO:80.

* * * * *

SEQUENCE LISTING

```
<160> NUMBER OF SEQ ID NOS: 88

<210> SEQ ID NO 1
<211> LENGTH: 39
<212> TYPE: DNA
<213> ORGANISM: Artificial
<220> FEATURE:
<223> OTHER INFORMATION: TCR-CDR3 sequence of tyrosinase-specific
      allorestricted T cell clone T58 alpha-chain: TRAV1-2 AJ28

<400> SEQUENCE: 1
tgtgctgtga catactctgg ggctgggagt taccaactc                              39

<210> SEQ ID NO 2
<211> LENGTH: 36
<212> TYPE: DNA
<213> ORGANISM: Artificial
<220> FEATURE:
<223> OTHER INFORMATION: TCR-CDR3 sequence of tyrosinase-specific
      allorestricted T cell clone T58 beta chain: TRBV13 BD1 BJ1-4

<400> SEQUENCE: 2
tgtgccagca gtcagaaaca gggctgggaa aaactg                                 36

<210> SEQ ID NO 3
<211> LENGTH: 39
<212> TYPE: DNA
<213> ORGANISM: Artificial
<220> FEATURE:
<223> OTHER INFORMATION: TCR-CDR3 sequence of tyrosinase-specific
      allorestricted T cell clone T43 alpha-chain: TRAV3 AJ28

<400> SEQUENCE: 3
tgtgctgtga gagaccctgg ggctgggagt taccaactc                              39

<210> SEQ ID NO 4
<211> LENGTH: 39
<212> TYPE: DNA
<213> ORGANISM: Artificial
```

<220> FEATURE:
<223> OTHER INFORMATION: TCR-CDR3 sequence of tyrosinase-specific
      allorestricted T cell clone T43 beta-chain: TRBV11-3 BD2 BJ2-1

<400> SEQUENCE: 4
tgtgccagca gcttagaacg ggagggaacc aatgagcag                           39

<210> SEQ ID NO 5
<211> LENGTH: 30
<212> TYPE: DNA
<213> ORGANISM: Artificial
<220> FEATURE:
<223> OTHER INFORMATION: TCR-CDR3 sequence of tyrosinase-specific
      allorestricted T cell clone Di111 alpha-chain 1: TRAV8-2 AJ20

<400> SEQUENCE: 5
tgtgttgtga gttctaacga ctacaagctc                                    30

<210> SEQ ID NO 6
<211> LENGTH: 42
<212> TYPE: DNA
<213> ORGANISM: Artificial
<220> FEATURE:
<223> OTHER INFORMATION: TCR-CDR3 sequence of tyrosinase-specific
      allorestricted T cell clone Di111 alpha-chain 2: TRAV3 AJ28

<400> SEQUENCE: 6
tgtgctgtga gagccctgg ggctgggagt taccaactca ct                       42

<210> SEQ ID NO 7
<211> LENGTH: 39
<212> TYPE: DNA
<213> ORGANISM: Artificial
<220> FEATURE:
<223> OTHER INFORMATION: TCR-CDR3 sequence of tyrosinase-specific
      allorestricted T cell clone Di111 beta-chain: TRBV18 BD2 BJ2-7

<400> SEQUENCE: 7
tgtgccagct caccttccga ggggtactcc tacgagcag                           39

<210> SEQ ID NO 8
<211> LENGTH: 42
<212> TYPE: DNA
<213> ORGANISM: Artificial
<220> FEATURE:
<223> OTHER INFORMATION: TCR-CDR3 sequence of tyrosinase-specific
      allorestricted T cell clone B12 alpha-chain 1: TRAV1-2 AJ38

<400> SEQUENCE: 8
tgtgctgtga gacccgttaa tgctggcaac aaccgtaagc tg                      42

<210> SEQ ID NO 9
<211> LENGTH: 39
<212> TYPE: DNA
<213> ORGANISM: Artificial
<220> FEATURE:
<223> OTHER INFORMATION: TCR-CDR3 sequence of tyrosinase-specific
      allorestricted T cell clone B12 alpha-chain 2: TRAV38-1 AJ28

<400> SEQUENCE: 9
tgtgctttca ttaactctgg ggctgggagt taccaactc                           39

<210> SEQ ID NO 10
<211> LENGTH: 42
<212> TYPE: DNA
<213> ORGANISM: Artificial
<220> FEATURE:

<223> OTHER INFORMATION: TCR-CDR3 sequence of tyrosinase-specific
allorestricted T cell clone B12 beta-chain: TRBV7-9 BD2 BJ2-3

<400> SEQUENCE: 10
tgtgccagca gctccattag cttacctagc acagatacgc ag        42

<210> SEQ ID NO 11
<211> LENGTH: 27
<212> TYPE: DNA
<213> ORGANISM: Artificial
<220> FEATURE:
<223> OTHER INFORMATION: TCR-CDR3 sequence of melan-A-specific
allorestricted T cell clone SW-M1-9 alpha-chain: TRAV12-2 AJ 40

<400> SEQUENCE: 11
tgtgccgtga ccggaaccta caaatac        27

<210> SEQ ID NO 12
<211> LENGTH: 42
<212> TYPE: DNA
<213> ORGANISM: Artificial
<220> FEATURE:
<223> OTHER INFORMATION: TCR-CDR3 sequence of melan-A-specific
allorestricted T cell clone SW-M1-9 beta-chain: TRBV3-1 BD2 BJ2-7

<400> SEQUENCE: 12
tgtgccagca gccccctggg actagcggag gtttccgagc ag        42

<210> SEQ ID NO 13
<211> LENGTH: 24
<212> TYPE: DNA
<213> ORGANISM: Artificial
<220> FEATURE:
<223> OTHER INFORMATION: TCR-CDR3 sequence of melan-A-specific
allorestricted T cell clone SW-M1-29 alpha-chain: TRAV30 AJ31

<400> SEQUENCE: 13
tgcggaggta acaatgccag actc        24

<210> SEQ ID NO 14
<211> LENGTH: 42
<212> TYPE: DNA
<213> ORGANISM: Artificial
<220> FEATURE:
<223> OTHER INFORMATION: TCR-CDR3 sequence of melan-A-specific
allorestricted T cell clone SW-M1-29 beta-chain: TRBV27 BD1 BJ2-2

<400> SEQUENCE: 14
tgtgccagca ggcccgggac aggaattttt gacggggagc tg        42

<210> SEQ ID NO 15
<211> LENGTH: 24
<212> TYPE: DNA
<213> ORGANISM: Artificial
<220> FEATURE:
<223> OTHER INFORMATION: TCR-CDR3 sequence of melan-A-specific
allorestricted T cell clone SW-M1-54 alpha-chain: TRAV12-2 AJ31

<400> SEQUENCE: 15
tgtgccccaa acaatgccag actc        24

<210> SEQ ID NO 16
<211> LENGTH: 48
<212> TYPE: DNA
<213> ORGANISM: Artificial
<220> FEATURE:
<223> OTHER INFORMATION: TCR-CDR3 sequence of melan-A-specific -continued allorestricted T cell clone SW-M1-54 beta-chain: TRBV12-3 BD2
BJ2-2

<400> SEQUENCE: 16
tgtgccagca gccccacgat cctggtggag gcgtacaccg gggagctg         48

<210> SEQ ID NO 17
<211> LENGTH: 24
<212> TYPE: DNA
<213> ORGANISM: Artificial
<220> FEATURE:
<223> OTHER INFORMATION: TCR-CDR3 sequence of melan-A-specific
      allorestricted T cell clone SW-M1-54 alpha-chain: TRAV12-2 AJ31

<400> SEQUENCE: 17
tgtgccgtcg ggggtgacaa gatc                                   24

<210> SEQ ID NO 18
<211> LENGTH: 33
<212> TYPE: DNA
<213> ORGANISM: Artificial
<220> FEATURE:
<223> OTHER INFORMATION: TCR-CDR3 sequence of melan-A-specific
      allorestricted T cell clone SW-M1-66 beta-chain: TRBV12-3 BD1
      BJ1-5

<400> SEQUENCE: 18
tgtgccagca gtttgggaca gggctggccc cag                         33

<210> SEQ ID NO 19
<211> LENGTH: 21
<212> TYPE: DNA
<213> ORGANISM: Artificial
<220> FEATURE:
<223> OTHER INFORMATION: TCR-CDR3 sequence of melan-A-specific
      allorestricted T cell clone SW-M1-67 alpha-chain: TRAV12-2 AJ29

<400> SEQUENCE: 19
tgtgccgtga ggacacctct t                                      21

<210> SEQ ID NO 20
<211> LENGTH: 36
<212> TYPE: DNA
<213> ORGANISM: Artificial
<220> FEATURE:
<223> OTHER INFORMATION: TCR-CDR3 sequence of melan-A-specific
      allorestricted T cell clone SW-M1-67 beta-chain: TRBV30 BD2 BJ2-1

<400> SEQUENCE: 20
tgtgcctgga gttcaagcgg tttgggcgtt gagcag                      36

<210> SEQ ID NO 21
<211> LENGTH: 39
<212> TYPE: DNA
<213> ORGANISM: Artificial
<220> FEATURE:
<223> OTHER INFORMATION: TCR-CDR3 sequence of survivin-specific
      allorestricted T cell clone SW-Surv-22 alpha-chain: TRAV20 AJ41

<400> SEQUENCE: 21
tgtgctgtgc aggcttactc aaattccggg tatgcactc                   39

<210> SEQ ID NO 22
<211> LENGTH: 27
<212> TYPE: DNA
<213> ORGANISM: Artificial
<220> FEATURE:

```
<223> OTHER INFORMATION: TCR-CDR3 sequence of survivin-specific
      allorestricted T cell clone SW-Surv-22 beta-chain: TRBV29-1 BD1
      BJ1-2

<400> SEQUENCE: 22
tgcagcgttg aagacagcta tggctac                                             27

<210> SEQ ID NO 23
<211> LENGTH: 27
<212> TYPE: DNA
<213> ORGANISM: Artificial
<220> FEATURE:
<223> OTHER INFORMATION: TCR-CDR3 sequence of survivin-specific
      allorestricted T cell clone SW-Surv-66 alpha-chain: TRAV13-1 AJ39

<400> SEQUENCE: 23
tgtgcagcaa gggcaggcaa catgctc                                             27

<210> SEQ ID NO 24
<211> LENGTH: 36
<212> TYPE: DNA
<213> ORGANISM: Artificial
<220> FEATURE:
<223> OTHER INFORMATION: TCR-CDR3 sequence of survivin-specific
      allorestricted T cell clone SW-Surv-66 beta-chain: TRBV30 BD2
      BJ2-7

<400> SEQUENCE: 24
tgtgcctggg gtacgggact agcgctttac gagcag                                   36

<210> SEQ ID NO 25
<211> LENGTH: 24
<212> TYPE: DNA
<213> ORGANISM: Artificial
<220> FEATURE:
<223> OTHER INFORMATION: TCR-CDR3 sequence of survivin-specific
      allorestricted T cell clone SW-Surv-71 alpha-chain: TRAV12-2 AJ31

<400> SEQUENCE: 25
tgtgccgtga acaatgccag actc                                                24

<210> SEQ ID NO 26
<211> LENGTH: 30
<212> TYPE: DNA
<213> ORGANISM: Artificial
<220> FEATURE:
<223> OTHER INFORMATION: TCR-CDR3 sequence of survivin-specific
      allorestricted T cell clone SW-Surv-71 beta-chain: TRBV30 BD2
      BJ2-1

<400> SEQUENCE: 26
tgtgcctgga gcataggcgc tgagcagttc                                          30

<210> SEQ ID NO 27
<211> LENGTH: 36
<212> TYPE: DNA
<213> ORGANISM: Artificial
<220> FEATURE:
<223> OTHER INFORMATION: TCR-CDR3 sequence of survivin-specific
      allorestricted T cell clone SW-Surv-72 alpha-chain: TRAV14 AJ4

<400> SEQUENCE: 27
tgtgcaatga gagagggcgg gggctacaat aagctg                                   36

<210> SEQ ID NO 28
<211> LENGTH: 30
<212> TYPE: DNA
```

-continued

```
<213> ORGANISM: Artificial
<220> FEATURE:
<223> OTHER INFORMATION: TCR-CDR3 sequence of survivin-specific
      allorestricted T cell clone SW-Surv-72 beta-chain: TRBV30 BD1
      BJ1-1

<400> SEQUENCE: 28
tgtgccggac aggatttgaa cactgaagct                                     30

<210> SEQ ID NO 29
<211> LENGTH: 13
<212> TYPE: PRT
<213> ORGANISM: Artificial
<220> FEATURE:
<223> OTHER INFORMATION: TCR-CDR3 sequence of tyrosinase-specific
      allorestricted T cell clone T58 alpha-chain: TRAV1-2 AJ28

<400> SEQUENCE: 29

Cys Ala Val Thr Tyr Ser Gly Ala Gly Ser Tyr Gln Leu
1               5                   10

<210> SEQ ID NO 30
<211> LENGTH: 12
<212> TYPE: PRT
<213> ORGANISM: Artificial
<220> FEATURE:
<223> OTHER INFORMATION: TCR-CDR3 sequence of tyrosinase-specific
      allorestricted T cell clone T58 beta chain: TRBV13 BD1 BJ1-4

<400> SEQUENCE: 30

Cys Ala Ser Ser Gln Lys Gln Gly Trp Glu Lys Leu
1               5                   10

<210> SEQ ID NO 31
<211> LENGTH: 13
<212> TYPE: PRT
<213> ORGANISM: Artificial
<220> FEATURE:
<223> OTHER INFORMATION: TCR-CDR3 sequence of tyrosinase-specific
      allorestricted T cell clone T43 alpha-chain: TRAV3 AJ28

<400> SEQUENCE: 31

Cys Ala Val Arg Asp Pro Gly Ala Gly Ser Tyr Gln Leu
1               5                   10

<210> SEQ ID NO 32
<211> LENGTH: 13
<212> TYPE: PRT
<213> ORGANISM: Artificial
<220> FEATURE:
<223> OTHER INFORMATION: TCR-CDR3 sequence of tyrosinase-specific
      allorestricted T cell clone T43 beta-chain: TRBV11-3 BD2 BJ2-1

<400> SEQUENCE: 32

Cys Ala Ser Ser Leu Glu Arg Glu Gly Thr Asn Glu Gln
1               5                   10

<210> SEQ ID NO 33
<211> LENGTH: 10
<212> TYPE: PRT
<213> ORGANISM: Artificial
<220> FEATURE:
<223> OTHER INFORMATION: TCR-CDR3 sequence of tyrosinase-specific
      allorestricted T cell clone Di111 alpha-chain 1: TRAV8-2 AJ20

<400> SEQUENCE: 33

Cys Val Val Ser Ser Asn Asp Tyr Lys Leu
1               5                   10
```

<210> SEQ ID NO 34
<211> LENGTH: 14
<212> TYPE: PRT
<213> ORGANISM: Artificial
<220> FEATURE:
<223> OTHER INFORMATION: TCR-CDR3 sequence of tyrosinase-specific
      allorestricted T cell clone Di111 alpha-chain 2: TRAV3 AJ28

<400> SEQUENCE: 34

Cys Ala Val Arg Asp Pro Gly Ala Gly Ser Tyr Gln Leu Thr
1               5                   10

<210> SEQ ID NO 35
<211> LENGTH: 13
<212> TYPE: PRT
<213> ORGANISM: Artificial
<220> FEATURE:
<223> OTHER INFORMATION: TCR-CDR3 sequence of tyrosinase-specific
      allorestricted T cell clone Di111 beta-chain: TRBV18 BD2 BJ2-7

<400> SEQUENCE: 35

Cys Ala Ser Ser Pro Ser Glu Gly Tyr Ser Tyr Glu Gln
1               5                   10

<210> SEQ ID NO 36
<211> LENGTH: 14
<212> TYPE: PRT
<213> ORGANISM: Artificial
<220> FEATURE:
<223> OTHER INFORMATION: TCR-CDR3 sequence of tyrosinase-specific
      allorestricted T cell clone B12 alpha-chain 1: TRAV1-2 AJ38

<400> SEQUENCE: 36

Cys Ala Val Arg Pro Val Asn Ala Gly Asn Asn Arg Lys Leu
1               5                   10

<210> SEQ ID NO 37
<211> LENGTH: 13
<212> TYPE: PRT
<213> ORGANISM: Artificial
<220> FEATURE:
<223> OTHER INFORMATION: TCR-CDR3 sequence of tyrosinase-specific
      allorestricted T cell clone B12 alpha-chain 2: TRAV38-1 AJ28

<400> SEQUENCE: 37

Cys Ala Phe Ile Asn Ser Gly Ala Gly Ser Tyr Gln Leu
1               5                   10

<210> SEQ ID NO 38
<211> LENGTH: 14
<212> TYPE: PRT
<213> ORGANISM: Artificial
<220> FEATURE:
<223> OTHER INFORMATION: TCR-CDR3 sequence of tyrosinase-specific
      allorestricted T cell clone B12 beta-chain: TRBV7-9 BD2 BJ2-3

<400> SEQUENCE: 38

Cys Ala Ser Ser Ser Ile Ser Leu Pro Ser Thr Asp Thr Gln
1               5                   10

<210> SEQ ID NO 39
<211> LENGTH: 9
<212> TYPE: PRT
<213> ORGANISM: Artificial
<220> FEATURE:
<223> OTHER INFORMATION: TCR-CDR3 sequence of melan-A-specific
      allorestricted T cell clone SW-M1-9 alpha-chain: TRAV12-2 AJ 40

-continued

<400> SEQUENCE: 39

Cys Ala Val Thr Gly Thr Tyr Lys Tyr
1               5

<210> SEQ ID NO 40
<211> LENGTH: 14
<212> TYPE: PRT
<213> ORGANISM: Artificial
<220> FEATURE:
<223> OTHER INFORMATION: TCR-CDR3 sequence of melan-A-specific
      allorestricted T cell clone SW-M1-9 beta-chain: TRBV3-1 BD2 BJ2-7

<400> SEQUENCE: 40

Cys Ala Ser Ser Pro Leu Gly Leu Ala Glu Val Ser Glu Gln
1               5                   10

<210> SEQ ID NO 41
<211> LENGTH: 8
<212> TYPE: PRT
<213> ORGANISM: Artificial
<220> FEATURE:
<223> OTHER INFORMATION: TCR-CDR3 sequence of melan-A-specific
      allorestricted T cell clone SW-M1-29 alpha-chain: TRAV30 AJ31

<400> SEQUENCE: 41

Cys Gly Gly Asn Asn Ala Arg Leu
1               5

<210> SEQ ID NO 42
<211> LENGTH: 14
<212> TYPE: PRT
<213> ORGANISM: Artificial
<220> FEATURE:
<223> OTHER INFORMATION: TCR-CDR3 sequence of melan-A-specific
      allorestricted T cell clone SW-M1-29 beta-chain: TRBV27 BD1 BJ2-2

<400> SEQUENCE: 42

Cys Ala Ser Arg Pro Gly Thr Gly Ile Phe Asp Gly Glu Leu
1               5                   10

<210> SEQ ID NO 43
<211> LENGTH: 8
<212> TYPE: PRT
<213> ORGANISM: Artificial
<220> FEATURE:
<223> OTHER INFORMATION: TCR-CDR3 sequence of melan-A-specific
      allorestricted T cell clone SW-M1-54 alpha-chain: TRAV12-2 AJ31

<400> SEQUENCE: 43

Cys Ala Pro Asn Asn Ala Arg Leu
1               5

<210> SEQ ID NO 44
<211> LENGTH: 16
<212> TYPE: PRT
<213> ORGANISM: Artificial
<220> FEATURE:
<223> OTHER INFORMATION: TCR-CDR3 sequence of melan-A-specific
      allorestricted T cell clone SW-M1-54 beta-chain: TRBV12-3 BD2
      BJ2-2

<400> SEQUENCE: 44

Cys Ala Ser Ser Pro Thr Ile Leu Val Glu Ala Tyr Thr Gly Glu Leu
1               5                   10                  15

<210> SEQ ID NO 45

```
<211> LENGTH: 8
<212> TYPE: PRT
<213> ORGANISM: Artificial
<220> FEATURE:
<223> OTHER INFORMATION: TCR-CDR3 sequence of melan-A-specific
      allorestricted T cell clone SW-M1-66 alpha-chain: TRAV12-2 AJ30

<400> SEQUENCE: 45

Cys Ala Val Gly Gly Asp Lys Ile
1               5

<210> SEQ ID NO 46
<211> LENGTH: 11
<212> TYPE: PRT
<213> ORGANISM: Artificial
<220> FEATURE:
<223> OTHER INFORMATION: TCR-CDR3 sequence of melan-A-specific
      allorestricted T cell clone SW-M1-66 beta-chain: TRBV12-3 BD1
      BJ1-5

<400> SEQUENCE: 46

Cys Ala Ser Ser Leu Gly Gln Gly Trp Pro Gln
1               5                   10

<210> SEQ ID NO 47
<211> LENGTH: 7
<212> TYPE: PRT
<213> ORGANISM: Artificial
<220> FEATURE:
<223> OTHER INFORMATION: TCR-CDR3 sequence of melan-A-specific
      allorestricted T cell clone SW-M1-67 alpha-chain: TRAV12-2 AJ29

<400> SEQUENCE: 47

Cys Ala Val Arg Thr Pro Leu
1               5

<210> SEQ ID NO 48
<211> LENGTH: 12
<212> TYPE: PRT
<213> ORGANISM: Artificial
<220> FEATURE:
<223> OTHER INFORMATION: TCR-CDR3 sequence of melan-A-specific
      allorestricted T cell clone SW-M1-67 beta-chain: TRBV30 BD2 BJ2-1

<400> SEQUENCE: 48

Cys Ala Trp Ser Ser Ser Gly Leu Gly Val Glu Gln
1               5                   10

<210> SEQ ID NO 49
<211> LENGTH: 13
<212> TYPE: PRT
<213> ORGANISM: Artificial
<220> FEATURE:
<223> OTHER INFORMATION: TCR-CDR3 sequence of survivin-specific
      allorestricted T cell clone SW-Surv-22 alpha-chain: TRAV20 AJ41

<400> SEQUENCE: 49

Cys Ala Val Gln Ala Tyr Ser Asn Ser Gly Tyr Ala Leu
1               5                   10

<210> SEQ ID NO 50
<211> LENGTH: 9
<212> TYPE: PRT
<213> ORGANISM: Artificial
<220> FEATURE:
<223> OTHER INFORMATION: TCR-CDR3 sequence of survivin-specific
      allorestricted T cell clone SW-Surv-22 beta-chain: TRBV29-1 BD1
      BJ1-2
```

```
<400> SEQUENCE: 50

Cys Ser Val Glu Asp Ser Tyr Gly Tyr
1               5

<210> SEQ ID NO 51
<211> LENGTH: 9
<212> TYPE: PRT
<213> ORGANISM: Artificial
<220> FEATURE:
<223> OTHER INFORMATION: TCR-CDR3 sequence of survivin-specific
      allorestricted T cell clone SW-Surv-66 alpha-chain: TRAV13-1 AJ39

<400> SEQUENCE: 51

Cys Ala Ala Arg Ala Gly Asn Met Leu
1               5

<210> SEQ ID NO 52
<211> LENGTH: 12
<212> TYPE: PRT
<213> ORGANISM: Artificial
<220> FEATURE:
<223> OTHER INFORMATION: TCR-CDR3 sequence of survivin-specific
      allorestricted T cell clone SW-Surv-66 beta-chain: TRBV30 BD2
      BJ2-7

<400> SEQUENCE: 52

Cys Ala Trp Gly Thr Gly Leu Ala Leu Tyr Glu Gln
1               5                   10

<210> SEQ ID NO 53
<211> LENGTH: 8
<212> TYPE: PRT
<213> ORGANISM: Artificial
<220> FEATURE:
<223> OTHER INFORMATION: TCR-CDR3 sequence of survivin-specific
      allorestricted T cell clone SW-Surv-71 alpha-chain: TRAV12-2 AJ31

<400> SEQUENCE: 53

Cys Ala Val Asn Asn Ala Arg Leu
1               5

<210> SEQ ID NO 54
<211> LENGTH: 10
<212> TYPE: PRT
<213> ORGANISM: Artificial
<220> FEATURE:
<223> OTHER INFORMATION: TCR-CDR3 sequence of survivin-specific
      allorestricted T cell clone SW-Surv-71 beta-chain: TRBV30 BD2
      BJ2-1

<400> SEQUENCE: 54

Cys Ala Trp Ser Ile Gly Ala Glu Gln Phe
1               5                   10

<210> SEQ ID NO 55
<211> LENGTH: 12
<212> TYPE: PRT
<213> ORGANISM: Artificial
<220> FEATURE:
<223> OTHER INFORMATION: TCR-CDR3 sequence of survivin-specific
      allorestricted T cell clone SW-Surv-72 alpha-chain: TRAV14 AJ4

<400> SEQUENCE: 55

Cys Ala Met Arg Glu Gly Gly Gly Tyr Asn Lys Leu
1               5                   10

<210> SEQ ID NO 56
```

<211> LENGTH: 10
<212> TYPE: PRT
<213> ORGANISM: Artificial
<220> FEATURE:
<223> OTHER INFORMATION: TCR-CDR3 sequence of survivin-specific
     allorestricted T cell clone SW-Surv-72 beta-chain: TRBV30 BD1
     BJ1-1

<400> SEQUENCE: 56

Cys Ala Gly Gln Asp Leu Asn Thr Glu Ala
1               5                   10

<210> SEQ ID NO 57
<211> LENGTH: 813
<212> TYPE: DNA
<213> ORGANISM: Artificial
<220> FEATURE:
<223> OTHER INFORMATION: tyrosinase-directed TCR alpha-chain T58 alpha
     (VJ region)

<400> SEQUENCE: 57
atgtggggag ttttccttct ttatgtttcc atgaagatgg gaggcactac aggacaaaac      60
attgaccagc ccactgagat gacagctacg gaaggtgcca ttgtccagat caactgcacg     120
taccagacat ctgggttcaa cgggctgttc tggtaccagc aacatgctgg cgaagcaccc     180
acatttctgt cttacaatgt tctggatggt ttggaggaga aggtcgtttt tcttcattc      240 cttagtcggt ctaaagggta cagttacctc cttttgaagg agctccagat gaaagactct     300
gcctcttacc tctgtgctgt gacatactct ggggctggga gttaccaact cactttcggg     360
aaggggacca aactctcggt cataccaaat atccagaacc ctgaccctgc cgtgtaccag     420
ctgagagact ctaaatccag tgacaagtct gtctgcctat tcaccgattt tgattctcaa     480
acaaatgtgt cacaaagtaa ggattctgat gtgtatatca cagacaaaac tgtgctagac     540
atgaggtcta tggacttcaa gagcaacagt gctgtggcct ggagcaacaa atctgacttt     600
gcatgtgcaa acgccttcaa caacagcatt attccagaag acaccttctt ccccagccca     660
gaaagttcct gtgatgtcaa gctggtcgag aaaagctttg aaacagatac gaacctaaac     720 tttcaaaaacc tgtcagtgat tgggttccga atcctcctcc tgaaagtggc cgggtttaat     780
ctgctcatga cgctgcggct gtggtccagc tga                                  813

<210> SEQ ID NO 58
<211> LENGTH: 957
<212> TYPE: DNA
<213> ORGANISM: Artificial
<220> FEATURE:
<223> OTHER INFORMATION: tyrosinase-directed TCR beta-chain T58 beta
     (VDJ region)

<400> SEQUENCE: 58
atgcttagtc ctgacctgcc tgactctgcc tggaacacca ggctcctctg ccatgtcatg      60
ctttgtctcc tgggagcagt ttcagtggct gctggagtca tccagtcccc aagacatctg     120
atcaaagaaa agaggcaaac agccactctg aaatgctatc ctatccctag acacgacact     180
gtctactggt accagcaggg tccaggtcag gaccccccagt tcctcatttc gttttatgaa     240
aagatgcaga gcgataaagg aagcatccct gatcgattct cagctcaaca gttcagtgac     300
tatcattctg aactgaacat gagctccttg gagctggggg actcagccct gtacttctgt     360
gccagcagtc agaaacaggg ctgggaaaaa ctgttttttg cagtggaac ccagctctct     420 gtcttggagg acctgaacaa ggtgttccca cccgaggtcg ctgtgtttga gccatcagaa     480

| | |
|---|---|
| gcagagatct cccacaccca aaaggccaca ctggtgtgcc tggccacagg cttcttccct | 540 |
| gaccacgtgg agctgagctg gtgggtgaat gggaaggagg tgcacagtgg ggtcagcacg | 600 |
| gacccgcagc ccctcaagga gcagcccgcc ctcaatgact ccagatactg cctgagcagc | 660 |
| cgcctgaggt ctcggccac cttctggcag aaccccgca accacttccg ctgtcaagtc | 720 |
| cagttctacg ggctctcgga gaatgacgag tggacccagg atagggccaa acccgtcacc | 780 |
| cagatcgtca gcgccgaggc ctggggtaga gcagactgtg gctttacctc ggtgtcctac | 840 |
| cagcaagggg tcctgtctgc caccatcctc tatgagatcc tgctagggaa ggccaccctg | 900 |
| tatgctgtgc tggtcagcgc ccttgtgttg atggccatgg tcaagagaaa ggatttc | 957 |

```
<210> SEQ ID NO 59
<211> LENGTH: 828
<212> TYPE: DNA
<213> ORGANISM: Artificial
<220> FEATURE:
<223> OTHER INFORMATION: tyrosinase-directed TCR alpha-chain T43 alpha
      (VJ region)

<400> SEQUENCE: 59
```

| | |
|---|---|
| atggcctctg cacccatctc gatgcttgcg atgctcttca cattgagtgg gctgagagct | 60 |
| cagtcagtgg ctcagccgga agatcaggtc aacgttgctg aagggaatcc tctgactgtg | 120 |
| aaatgcacct attcagtctc tggaaaccct tatcttttt ggtatgttca ataccccaac | 180 |
| cgaggcctcc agttccttct gaaatacatc acaggggata acctggttaa aggcagctat | 240 |
| ggctttgaag ctgaatttaa caagagccaa acctccttcc acctgaagaa accatctgcc | 300 |
| cttgtgagcg actccgcttt gtacttctgt gctgtgagag accctggggc tgggagttac | 360 |
| caactcactt tcgggaaggg gaccaaactc tcggtcatac aaatatcca gaaccctgac | 420 |
| cctgccgtgt accagctgag agactctaaa tccagtgaca agtctgtctg cctattcacc | 480 |
| gattttgatt ctcaaacaaa tgtgtcacaa agtaaggatt ctgatgtgta tatcacagac | 540 |
| aaaactgtgc tagacatgag gtcatggac ttcaagagca cagtgctgt ggcctggagc | 600 |
| aacaaatctg acttcgcatg tgcaaacgcc ttcaacaaca gcattattcc agaagacacc | 660 |
| ttcttcccca gcccagaaag ttcctgtgat gtcaagctgg tcgagaaaag ctttgaaaca | 720 |
| gatacgaacc taaactttca aaacctgtca gtgattgggt tccgaatcct cctcctgaaa | 780 |
| gtggccgggt taatctgct catgacgctg cggctgtggt ccagctga | 828 |

```
<210> SEQ ID NO 60
<211> LENGTH: 939
<212> TYPE: DNA
<213> ORGANISM: Artificial
<220> FEATURE:
<223> OTHER INFORMATION: tyrosinase-directed TCR beta-chain T43 beta
      (VDJ region)

<400> SEQUENCE: 60
```

| | |
|---|---|
| atgggtacca ggctcctctg ctgggtggcc ttctgtctcc tgtggaaga actcatagaa | 60 |
| gctggagtgg ttcagtctcc cagatataag attatagaga aaaacagcc tgtggctttt | 120 |
| tggtgcaatc ctatttctgg ccacaatacc ctttactggt acctgcagaa cttgggacag | 180 |
| ggcccggagc ttctgattcg atatgagaat gaggaagcag tagacgattc acagttgcct | 240 |
| aaggatcgat tttctgcaga gaggctcaaa ggagtagact ccactctcaa gatccagcct | 300 |
| gcagagcttg ggactcggc cgtgtatctc tgtgccagca gcttagaacg ggagggaacc | 360 |
| aatgagcagt tcttcgggcc aggacacgg ctcaccgtgc tagaggacct gaaaaacgtg | 420 |

-continued

```
ttcccacccg aggtcgctgt gtttgagcca tcagaagcag agatctccca cacccaaaag    480
gccacactgg tgtgcctggc cacaggcttc taccccgacc acgtggagct gagctggtgg    540
gtgaatggga aggaggtgca cagtggggtc agcacagacc cgcagcccct caaggagcag    600
cccgccctca atgactccag atactgcctg agcagccgcc tgagggtctc ggccaccttc    660
tggcagaacc cccgcaacca cttccgctgt caagtccagt tctacgggct ctcggagaat    720
gacgagtgga cccaggatag ggccaaacct gtcacccaga tcgtcagcgc cgaggcctgg    780
ggtagagcag actgtggctt cacctccgag tcttaccagc aaggggtcct gtctgccacc    840
atcctctatg agatcttgct agggaaggcc accttgtatg ccgtgctggt cagtgccctc    900
gtgctgatgg ccatggtcaa gagaaaggat tccagaggc                           939
```

<210> SEQ ID NO 61
<211> LENGTH: 819
<212> TYPE: DNA
<213> ORGANISM: Artificial
<220> FEATURE:
<223> OTHER INFORMATION: tyrosinase-directed TCR alpha-chain Di111 alpha chain 1 (VJ region)

<400> SEQUENCE: 61

```
atgctcctgc tgctcgtccc agtgctcgag gtgattttta ctctgggagg aaccagagcc    60
cagtcggtga cccagcttga cagccacgtc tctgtctctg aaggaacccc ggtgctgctg    120
aggtgcaact actcatcttc ttattcaccg tctctcttct ggtatgtgca accccaac     180 aaaggactcc agcttctcct gaagtacaca tcagcggcca cctggttaa aggtatcaac    240 ggttttgagg ctgaatttaa gaagagtgaa acctccttcc acctgacgaa accctcagcc    300
catatgagcg acgcggctga gtacttctgt gttgtgagtt ctaacgacta caagctcagc    360
tttggagccg gaaccacagt aactgtaaga gcaaatatcc agaaccctga ccctgccgtg    420
taccagctga gagactctaa atccagtgac aagtctgtct gcctattcac cgattttgat    480
tctcaaacaa atgtgtcaca aagtaaggat tctgatgtgt atatcacaga caaaactgtg    540
ctagacatga ggtctatgga cttcaagagc aacagtgctg tggcctggag caacaaatct    600
gactttgcat gtgcaaacgc cttcaacaac agcattattc agaagacac cttcttcccc    660 agcccagaaa gttcctgtga tgtcaagctg gtcgagaaaa gctttgaaac agatacgaac    720
ctaaactttc aaaacctgtc agtgattggg ttccgaatcc tcctcctgaa agtggccggg    780
tttaatctgc tcatgacgct gcggctgtgg tccagctga                           819
```

<210> SEQ ID NO 62
<211> LENGTH: 828
<212> TYPE: DNA
<213> ORGANISM: Artificial
<220> FEATURE:
<223> OTHER INFORMATION: tyrosinase-directed TCR alpha-chain Di111 alpha chain 2 (VJ region)

<400> SEQUENCE: 62

```
atggcctctg cacccatctc gatgcttgcg atgctcttca cattgagtgg gctgagagct    60
cagtcagtgg ctcagccgga agatcaggtc aacgttgctg aagggaatcc tctgactgtg    120
aaatgcacct attcagtctc tggaaacccct tatctttttt ggtatgttca ataccccaac    180
cgaggcctcc agttccttct gaaatacatc acagggggata acctggttaa aggcagctat    240 ggcttttgaag ctgaatttaa caagagccaa acctccttcc acctgaagaa accatctgcc    300
```

-continued

```
cttgtgagcg actccgcttt gtacttctgt gctgtgagag accctggggc tgggagttac    360
caactcactt tcgggaaggg gaccaaactc tcggtcatac caaatatcca gaaccctgac    420
cctgccgtgt accagctgag agactctaaa tccagtgaca agtctgtctg cctattcacc    480
gattttgatt ctcaaacaaa tgtgtcacaa agtaaggatt ctgatgtgta tatcacagac    540
aaaactgtgc tagacatgag gtctatggac ttcaagagca cagtgctgt ggcctggagc     600 aacaaatctg actttgcatg tgcaaacgcc ttcaacaaca gcattattcc agaagacacc    660
ttcttcccca gcccagaaag ttcctgtgat gtcaagctgg tcgagaaaag ctttgaaaca    720
gatacgaacc taaactttca aaacctgtca gtgattgggt tccgaatcct cctcctgaaa    780
gtggccgggt taatctgct catgacgctg cggctgtggt ccagctga                  828
```

<210> SEQ ID NO 63
<211> LENGTH: 941
<212> TYPE: DNA
<213> ORGANISM: Artificial
<220> FEATURE:
<223> OTHER INFORMATION: tyrosinase-directed TCR beta-chain Di111 beta
      chain (VDJC2*02)

<400> SEQUENCE: 63

```
atggacacca gagtactctg ctgtgcggtc atctgtcttc tgggggcagg tctctcaaat    60
gccggcgtca tgcagaaccc aagacacctg gtcaggagga ggggacagga ggcaagactg   120
agatgcagcc caatgaaagg cacacagtcat gtttactggt atcggcagct cccagaggaa   180
ggtctgaaat tcatggtttta tctccagaaa gaaaatatca tagatgagtc aggaatgcca   240
aaggaacgat tttctgctga atttcccaaa gagggcccca gcatcctgag gatccagcag   300
gtagtgcgag gagattcggc agcttatttc tgtgccagct caccttccga ggggtactcc   360
tacgagcagt acttcgggcc gggcaccagg ctcacggtca cagaggacct gaaaaacgtg   420
ttcccacccg aggtcgctgt gtttgagcca tcagaagcag atctcccca cacccaaaag   480 gccacactgg tatgcctggc cacaggcttc taccccgacc acgtggagct gagctggtgg   540
gtgaatggga aggaggtgca cagtgggggtc agcacagacc cgcagccct caaggagcag    600 cccgccctca atgactccag atactgcctg agcagccgcc tgagggtctc ggccaccttc    660
tggcagaacc ccgcaacca cttccgctgt caagtccagt tctacgggct ctcggagaat    720
gacgagtgga cccaggatag ggccaaaccc gtcacccaga tcgtcagcgc cgaggcctgg   780
ggtagagcag actgtggctt cacctccgag tcttaccagc aaggggtcct gtctgccacc   840
atcctctatg agatcttgct agggaaggcc accttgtatg ccgtgctggt cagtgccctc   900
gtgctgatgg ccatggtgtc aagagaaagg attccagagg c                       941
```

<210> SEQ ID NO 64
<211> LENGTH: 816
<212> TYPE: DNA
<213> ORGANISM: Artificial
<220> FEATURE:
<223> OTHER INFORMATION: tyrosinase-directed TCR alpha-chain B12 alpha
      chain 1 (VJ region)

<400> SEQUENCE: 64

```
atgtggggag ttttccttct ttatgtttcc atgaagatgg gaggcactac aggacaaaac    60
attgaccagc ccactgagat gacagctacg gaaggtgcca ttgtccagat caactgcacg   120
taccagacat ctgggttcaa cgggctgttc tggtaccagc aacatgctgg cgaagcacct   180
acatttctgt cttacaatgt tctggatggt ttggaggaga aggtcgtttt tcttcattc    240
```

```
cttagtcggt ctaaagggta cagttacctc cttttgaagg agctccagat gaaagactct    300
gcctcttacc tctgtgctgt gagacccgtt aatgctggca caaccgtaa gctgatttgg    360 ggattgggaa caagcctggc agtaaatccg aatatccaga accctgaccc tgccgtgtac    420
cagctgagag actctaaatc cagtgacaag tctgtctgcc tattcaccga ttttgattct    480
caaacaaatg tgtcacaaag taaggattct gatgtgtata tcacagacaa aactgtgcta    540
gacatgaggt ctatggactt caagagcaac agtgctgtgg cctggagcaa caaatctgac    600
tttgcatgtg caaacgcctt caacaacagc attattccag aagacacctt cttccccagc    660
ccagaaagtt cctgtgatgt caagctggtc gagaaaagct ttgaaacaga tacgaaccta    720
aactttcaaa acctgtcagt gattgggttc cgaatcctcc tcctgaaagt ggccgggttt    780
aatctgctca tgacgctgcg gctgtggtcc agctga                              816

<210> SEQ ID NO 65
<211> LENGTH: 834
<212> TYPE: DNA
<213> ORGANISM: Artificial
<220> FEATURE:
<223> OTHER INFORMATION: B12 alpha chain 2 (VJC)
<220> FEATURE:
<223> OTHER INFORMATION: tyrosinase-directed TCR alpha-chain B12 alpha
      chain 2 (VJ region)

<400> SEQUENCE: 65
atgacacgag ttagcttgct gtgggcagtc gtggtctcca cctgtcttga atccggcatg     60
gcccagacag tcactcagtc tcaaccagag atgtctgtgc aggaggcaga gactgtgacc    120
ctgagttgca catatgacac cagtgagaat aattattatt tgttctggta caagcagcct    180
cccagcaggc agatgattct cgttattcgc caagaagctt ataagcaaca gaatgcaacg    240
gagaatcgtt tctctgtgaa cttccagaaa gcagccaaat ccttcagtct caagatctca    300
gactcacagc tgggggacac tgcgatgtat ttctgtgctt tcattaactc tggggctggg    360
agttaccaac tcactttcgg gaaggggacc aaactctcgg tcataccaaa tatccagaac    420
cctgaccctg ccgtgtacca gctgagagac tctaaatcca gtgacaagtc tgtctgccta    480
ttcaccgatt ttgattctca aacaaatgtg tcacaaagta aggattctga tgtgtatatc    540
acagacaaaa ctgtgctaga catgaggtct atggacttca gagcaacag tgctgtggcc    600 tggagcaaca aatctgactt tgcatgtgca aacgccttca acaacagcat tattccagaa    660
gacaccttct tccccagccc agaaagttcc tgtgatgtca agctggtcga gaaaagcttt    720
gaaacagata cgaacctaaa ctttcaaaac ctgtcagtga ttgggttccg aatcctcctc    780
ctgaaagtgg ccgggtttaa tctgctcatg acgctgcggc tgtggtccag ctga          834

<210> SEQ ID NO 66
<211> LENGTH: 942
<212> TYPE: DNA
<213> ORGANISM: Artificial
<220> FEATURE:
<223> OTHER INFORMATION: tyrosinase-directed TCR beta-chain B12 beta
      chain (VDJ region)

<400> SEQUENCE: 66
atgggcacca gcctcctctg ctggatggcc ctgtgtctcc tggggcaga tcacgcagat     60 actggagtct cccagaaccc cagacacaag atcacaaaga ggggacagaa tgtaactttc    120
aggtgtgatc caatttctga acacaaccgc ctttattggt accgacagac cctggggcag    180
```

```
ggcccagagt tctgactta cttccagaat gaagctcaac tagaaaaatc aaggctgctc      240
agtgatcggt tctctgcaga gaggcctaag ggatctttct ccaccttgga gatccagcgc      300
acagagcagg gggactcggc catgtatctc tgtgccagca gctccattag cttacctagc      360
acagatacgc agtattttgg cccaggcacc cggctgacag tgctcgagga cctgaaaaac      420
gtgttcccac ccgaggtcgc tgtgtttgag ccatcagaag cagagatctc ccacacccaa      480
aaggccacac tggtgtgcct ggccacaggc ttctaccccg accacgtgga gctgagctgg      540
tgggtgaatg gaaggaggt gcacagtggg gtcagcacag acccgcagcc cctcaaggag      600
cagcccgccc tcaatgactc cagatactgc ctgagcagcc gcctgagggt ctcggccacc      660
ttctggcaga accccgcaa ccacttccgc tgtcaagtcc agttctacgg gctctcggag      720
aatgacgagt ggaccaggga tagggccaaa cctgtcaccc agatcgtcag cgccgaggcc      780
tggggtagag cagactgtgg cttcacctcc gagtcttacc agcaaggggt cctgtctgcc      840
accatcctct atgagatctt gctagggaag gccaccttgt atgccgtgct ggtcagtgcc      900
ctcgtgctga tggccatggt caagagaaag gattccagag gc                        942

<210> SEQ ID NO 67
<211> LENGTH: 816
<212> TYPE: DNA
<213> ORGANISM: Artificial
<220> FEATURE:
<223> OTHER INFORMATION: SW-M1-9 alpha chain (VJC)
<220> FEATURE:
<223> OTHER INFORMATION: melan-A-directed TCR alpha-chain SW-M1-9 alpha
      chain (VJ region)

<400> SEQUENCE: 67
atgaaatcct tgagagtttt actagtgatc ctgtggcttc agttgagctg ggtttggagc       60
caacagaagg aggtggagca gaattctgga cccctcagtg ttccagaggg agccattgcc      120
tctctcaact gcacttacag tgaccgaggt tcccagtcct tcttctggta cagacaatat      180
tctgggaaaa gccctgagtt gataatgttc atatactcca atggtgacaa agaagatgga      240
aggtttacag cacagctcaa taaagccagc cagtatgttt ctctgctcat cagagactcc      300
cagcccagtg attcagccac ctacctctgt gccgtgaccg aacctacaa atacatcttt      360 ggaacaggca ccaggctgaa ggttttagca aatatccaga cccctgaccc tgccgtgtac      420
cagctgagag actctaaatc cagtgacaag tctgtctgcc tattcaccga ttttgattct      480
caaacaaatg tgtcacaaag taaggattct gatgtgtata tcacagacaa aactgtgcta      540
gacatgaggt ctatggactt caagagcaac agtgctgtgg cctggagcaa caaatctgac      600
tttgcatgtg caaacgcctt caacaacagc attattccag aagacacctt cttccccagc      660
ccagaaagtt cctgtgatgt caagctggtc gagaaaagct ttgaaacaga tacgaaccta      720
aactttcaaa acctgtcagt gattgggttc cgaatcctcc tcctgaaagt ggccgggttt      780
aatctgctca tgacgctgcg gctgtggtcc agctga                               816

<210> SEQ ID NO 68
<211> LENGTH: 939
<212> TYPE: DNA
<213> ORGANISM: Artificial
<220> FEATURE:
<223> OTHER INFORMATION: melan-A-directed TCR alpha-chain SW-M1-9 beta
      chain (VDJ region)

<400> SEQUENCE: 68
atgggctgca ggctcctctg ctgtgtggtc ttctgcctcc tccaagcagg tccccttggac      60
```

```
acagctgttt cccagactcc aaaatacctg gtcacacaga tgggaaacga caagtccatt      120
aaatgtgaac aaaatctggg ccatgatact atgtattggt ataaacagga ctctaagaaa      180
tttctgaaga taatgtttag ctacaataat aaggagctca ttataaatga aacagttcca      240
aatcgcttct cacctaaatc tccagacaaa gctcacttaa atcttcacat caattccctg      300
gagcttggtg actctgctgt gtatttctgt gccagcagcc cctgggact agcggaggtt       360 tccgagcagt acttcgggcc gggcaccagg ctcacggtca cagaggacct gaaaacgtg       420 ttcccacccg aggtcgctgt gtttgagcca tcagaagcag atctcccca cccaaaag        480 gccacactgg tgtgcctggc acaggcttc taccccgacc acgtgagct gagctggtgg        540 gtgaatggga aggaggtgca cagtgggtc agcacagacc cgcagccct caaggagcag       600 cccgccctca atgactccag atactgcctg agcagccgcc tgagggtctc ggccaccttc      660
tggcagaacc cccgcaacca cttccgctgt caagtccagt tctacgggct ctcggagaat      720
gacgagtgga cccaggatag ggccaaacct gtcacccaga tcgtcagcgc cgaggcctgg      780
ggtagagcag actgtggctt cacctccgag tcttaccagc aaggggtcct gtctgccacc      840
atcctctatg agatcttgct agggaaggcc accttgtatg ccgtgctggt cagtgccctc      900
gtgctgatgg ccatggtcaa gagaaaggat tccagaggc                            939

<210> SEQ ID NO 69
<211> LENGTH: 810
<212> TYPE: DNA
<213> ORGANISM: Artificial
<220> FEATURE:
<223> OTHER INFORMATION: melan-A-directed TCR alpha-chain SW-M1-29 alpha
      chain (VJ region)

<400> SEQUENCE: 69
atggagactc tcctgaaagt gctttcaggc accttgttgt ggcagttgac ctgggtgaga       60
agccaacaac cagtgcagag tcctcaagcc gtgatcctcc gagaagggga agatgctgtc      120
atcaactgca gttcctccaa ggctttatat tctgtacact ggtacaggca gaagcatggt      180
gaagcacccg tcttcctgat gatattactg aagggtggag aacagaaggg tcatgaaaaa      240
atatctgctt catttaatga aaaaaagcag caaagctccc tgtaccttac ggcctcccag      300
ctcagttact caggaaccta cttctgcgga ggtaacaatg ccagactcat gtttggagat      360
ggaactcagc tggtggtgaa gcccaatatc agaaccctg accctgccgt gtaccagctg       420
agagactcta atccagtga caagtctgtc tgcctattca ccgatttga ttctcaaaca        480 aatgtgtcac aaagtaagga ttctgatgtg tatatcacag acaaaactgt gctagacatg      540
aggtctatgg acttcaagag caacagtgct gtggcctgga gcaacaaatc tgactttgca      600
tgtgcaaacg ccttcaacaa cagcattatt ccagaagaca ccttcttccc cagcccagaa      660
agttcctgtg atgtcaagct ggtcgagaaa agctttgaaa cagatacgaa cctaaacttt      720
caaaacctgt cagtgattgg gttccgaatc ctcctcctga agtggccgg gtttaatctg       780 ctcatgacgc tgcggctgtg gtccagctga                                      810

<210> SEQ ID NO 70
<211> LENGTH: 939
<212> TYPE: DNA
<213> ORGANISM: Artificial
<220> FEATURE:
<223> OTHER INFORMATION: melan-A-directed TCR beta-chain SW-M1-29 beta
      chain (VDJ region)
```

<400> SEQUENCE: 70

```
atgggccccc agctccttgg ctatgtggtc ctttgccttc taggagcagg cccctggaa      60
gcccaagtga cccagaaccc aagataccto atcacagtga ctggaaagaa gttaacagtg    120
acttgttctc agaatatgaa ccatgagtat atgtcctggt atcgacaaga cccagggctg    180
ggcttaaggc agatctacta ttcaatgaat gttgaggtga ctgataaggg agatgttcct    240
gaagggtaca aagtctctcg aaaagagaag aggaatttcc ccctgatcct ggagtcgccc    300
agccccaacc agacctctct gtacttctgt gccagcaggc ccgggacagg aattttttgac    360
ggggagctgt tttttggaga aggctctagg ctgaccgtac tggaggacct gaaaaacgtg    420
ttcccacccg aggtcgctgt gtttgagcca tcagaagcag agatctccca cacccaaaag    480
gccacactgg tgtgcctggc cacaggcttc taccccgacc acgtggagct gagctggtgg    540
gtgaatggga aggaggtgca cagtggggtc agcacagacc cgcagcccct caaggagcag    600
cccgccctca tgactccaga atactgcctg agcagccgcc tgagggtctc ggccaccttc    660
tggcagaacc ccgcaacca cttccgctgt caagtccagt tctacgggct ctcggagaat    720
gacgagtgga cccaggatag ggccaaacct gtcacccaga tcgtcagcgc cgaggcctgg    780
ggtagagcag actgtggctt cacctccgag tcttaccagc aagggggtcct gtctgccacc    840
atcctctatg agatcttgct agggaaggcc accttgtatg ccgtgctggt cagtgccctc    900
gtgctgatgg ccatggtcaa gagaaaggat tccagaggc                          939
```

<210> SEQ ID NO 71
<211> LENGTH: 813
<212> TYPE: DNA
<213> ORGANISM: Artificial
<220> FEATURE:
<223> OTHER INFORMATION: melan-A-directed TCR alpha-chain SW-M1-54 alpha
      chain (VJ region)

<400> SEQUENCE: 71

```
atgaaatcct tgagagtttt actagtgatc ctgtggcttc agttgagctg ggtttggagc      60
caacagaagg aggtggagca gaattctgga cccctcagtg ttccagaggg agccattgcc    120
tctctcaact gcacttacag tgaccgaggt tcccagtcct tcttctggta cagacaatat    180
tctgggaaaa gccctgagtt gataatgttc atatactcca atggtgacaa agaagatgga    240
aggtttacag cacagctcaa taagccagc cagtatgttt ctctgctcat cagagactcc    300
cagcccagtg attcagccac ctacctctgt gccccaaaca atgccagact catgtttgga    360
gatggaactc agctggtggt gaagcccaat atccagaacc ctgacctgc cgtgtaccag    420
ctgagagact ctaaatccag tgacaagtct gtctgcctat tcaccgattt tgattctcaa    480
acaaatgtgt cacaaagtaa ggattctgat gtgtatatca cagacaaaac tgtgctagac    540
atgaggtcta tggacttcaa gagcaacagt gctgtggcct ggagcaacaa atctgacttt    600
gcatgtgcaa acgccttcaa caacagcatt attccagaag acaccttctt ccccagccca    660
gaaagttcct gtgatgtcaa gctggtcgag aaaagctttg aaacagatac gaacctaaac    720
tttcaaaacc tgtcagtgat tgggttccga atcctcctcc tgaaagtggc cgggtttaat    780
ctgctcatga cgctgcggct gtggtccagc tga                                 813
```

<210> SEQ ID NO 72
<211> LENGTH: 948
<212> TYPE: DNA
<213> ORGANISM: Artificial
<220> FEATURE:

<223> OTHER INFORMATION: melan-A-directed TCR beta-chain SW-M1-54 beta
      chain (VDJ region)

<400> SEQUENCE: 72

```
atggactcct ggaccttctg ctgtgtgtcc ctttgcatcc tggtagcgaa gcatacagat      60
gctggagtta tccagtcacc ccgccatgag gtgacagaga tgggacaaga agtgactctg     120
agatgtaaac caatttcagg ccacaactcc cttttctggt acagacagac catgatgcgg     180
ggactggagt tgctcattta ctttaacaac aacgttccga tagatgattc agggatgccc     240
gaggatcgat tctcagctaa gatgcctaat gcatcattct ccactctgaa gatccagccc     300
tcagaaccca gggactcagc tgtgtacttc tgtgccagca gccccacgat cctggtggag     360
gcgtacaccg gggagctgtt ttttggagaa ggctctaggc tgaccgtact ggaggacctg     420
aaaaacgtgt tcccacccga ggtcgctgtg tttgagccat cagaagcaga gatctcccac     480
acccaaaagg ccacactggt gtgcctggcc acaggcttct accccgacca cgtggagctg     540
agctggtggg tgaatgggaa ggaggtgcac agtggggtca gcacagaccc gcagcccctc     600
aaggagcagc ccgccctcaa tgactccaga tactgcctga gcagccgcct gagggtctcg     660
gccaccttct ggcagaaccc ccgcaaccac ttccgctgtc aagtccagtt ctacgggctc     720
tcggagaatg acgagtggac ccaggatagg gccaaacctg tcacccagat cgtcagcgcc     780
gaggcctggg gtagagcaga ctgtggcttc acctccgagt cttaccagca aggggtcctg     840
tctgccacca tcctctatga gatcttgcta gggaaggcca ccttgtatgc cgtgctggtc     900
agtgccctcg tgctgatggc catggtcaag agaaaggatt ccagaggc                  948
```

<210> SEQ ID NO 73
<211> LENGTH: 813
<212> TYPE: DNA
<213> ORGANISM: Artificial
<220> FEATURE:
<223> OTHER INFORMATION: melan-A-directed TCR alpha-chain SW-M1-66 alpha
      chain (VJ region)

<400> SEQUENCE: 73

```
atgaaatcct tgagagtttt actagtgatc ctgtggcttc agttgagctg ggtttggagc      60
caacagaagg aggtggagca gaattctgga cccctcagtg ttccagaggg agccattgcc     120
tctctcaact gcacttacag tgaccgaggt tcccagtcct tcttctggta cagacaatat     180
tctgggaaaa gccctgagtt gataatgttc atatactcca atggtgacaa agaagatgga     240
aggtttacag cacagctcaa taaagccagc cagtatgttt ctctgctcat cagagactcc     300
cagcccagtg attcagccac ctacctctgt gccgtcgggg gtgacaagat catctttgga     360
aaagggacac gacttcatat tctccccaat atccagaacc ctgaccctgc cgtgtaccag     420
ctgagagact ctaaatccag tgacaagtct gtctgcctat tcaccgattt tgattctcaa     480
acaaatgtgt cacaaagtaa ggattctgat gtgtatatca cagacaaaac tgtgctagac     540
atgaggtcta tggacttcaa gagcaacagt gctgtggcct ggagcaacaa atctgacttt     600
gcatgtgcaa acgccttcaa caacagcatt attccagaag acaccttctt ccccagccca     660
gaaagttcct gtgatgtcaa gctggtcgag aaaagctttg aaacagatac gaacctaaac     720
tttcaaaacc tgtcagtgat tgggttccga atcctcctcc tgaaagtggc cgggtttaat     780
ctgctcatga cgctgcggct gtggtccagc tga                                  813
```

<210> SEQ ID NO 74
<211> LENGTH: 927

```
<212> TYPE: DNA
<213> ORGANISM: Artificial
<220> FEATURE:
<223> OTHER INFORMATION: melan-A-directed TCR beta-chain SW-M1-66 beta
      chain (VDJ region)

<400> SEQUENCE: 74
atggactcct ggaccttctg ctgtgtgtcc ctttgcatcc tggtagcgaa gcatacagat      60
gctggagtta tccagtcacc ccgccatgag gtgacagaga tgggacaaga agtgactctg     120
agatgtaaac caatttcagg ccacaactcc cttttctggt acagacagac catgatgcgg     180
ggactggagt tgctcattta ctttaacaac aacgttccga tagatgattc agggatgccc     240
gaggatcgat tctcagctaa gatgcctaat gcatcattct ccactctgaa gatccagccc     300
tcagaaccca gggactcagc tgtgtacttc tgtgccagca gtttgggaca gggctggccc     360
cagcattttg gtgatgggac tcgactctcc atcctagagg acctgaacaa ggtgttccca     420
cccgaggtcg ctgtgtttga gccatcagaa gcagagatct cccacaccca aaaggccaca     480
ctggtgtgcc tggccacagg cttcttccct gaccacgtgg agctgagctg gtgggtgaat     540
gggaaggagg tgcacagtgg ggtcagcacg gacccgcagc ccctcaagga gcagcccgcc     600
ctcaatgact ccagatactg cctgagcagc cgcctgaggg tctcggccac cttctggcag     660 aaccccgca accacttccg ctgtcaagtc cagttctacg gctctcgga gaatgacgag      720 tggacccagg atagggccaa acccgtcacc cagatcgtca gcgccgaggc ctggggtaga     780
gcagactgtg gctttacctc ggtgtcctac cagcaagggg tcctgtctgc caccatcctc     840
tatgagatcc tgctagggaa ggccaccctg tatgctgtgc tggtcagcgc ccttgtgttg     900
atggccatgg tcaagagaaa ggatttc                                         927

<210> SEQ ID NO 75
<211> LENGTH: 810
<212> TYPE: DNA
<213> ORGANISM: Artificial
<220> FEATURE:
<223> OTHER INFORMATION: melan-A-directed TCR alpha-chain SW-M1-67 alpha
      chain (VJ region)

<400> SEQUENCE: 75
atgaaatcct tgagagtttt actagtgatc ctgtggcttc agttgagctg ggtttggagc      60
caacagaagg aggtggagca gaattctgga cccctcagtg ttccagaggg agccattgcc     120
tctctcaact gcacttacag tgaccgaggt tcccagtcct tcttctggta cagacaatat     180
tctgggaaaa gccctgagtt gataatgttc atatactcca atggtgacaa agaagatgga     240
aggtttacag cacagctcaa taaagccagc cagtatgttt ctctgctcat cagagactcc     300
cagcccagtg attcagccac ctacctctgt gccgtgagga cacctcttgt ctttggaaag     360
ggcacaagac tttctgtgat tgcaaatatc cagaaccctg accctgccgt gtaccagctg     420
agagactcta atccagtgca agtctgtctg ccctattca ccgattttga ttctcaaaca     480
aatgtgtcac aaagtaagga ttctgatgtg tatatcacag acaaaactgt gctagacatg     540
aggtctatgg acttcaagag caacagtgct gtggcctgga gcaacaaatc tgactttgca     600
tgtgcaaacg ccttcaacaa cagcattatt ccagaagaca ccttcttccc cagcccagaa     660
agttcctgtg atgtcaagct ggtcgagaaa agctttgaaa cagatacgaa cctaaacttt     720
caaaacctgt cagtgattgg gttccgaatc ctcctcctga aagtggccgg gtttaatctg     780
ctcatgacgc tgcggctgtg gtccagctga                                      810
```

<210> SEQ ID NO 76
<211> LENGTH: 927
<212> TYPE: DNA
<213> ORGANISM: Artificial
<220> FEATURE:
<223> OTHER INFORMATION: melan-A-directed TCR beta-chain SW-M1-67 beta chain (VDJ region)

<400> SEQUENCE: 76

```
atgctctgct ctctccttgc ccttctcctg ggcactttct ttggggtcag atctcagact      60
attcatcaat ggccagcgac cctggtgcag cctgtgggca gcccgctctc tctggagtgc     120
actgtggagg aacatcaaa ccccaaccta tactggtacc gacaggctgc aggcaggggc     180
ctccagctgc tcttctactc cgttggtatt ggccagatca gctctgaggt gccccagaat     240
ctctcagcct ccagacccca ggaccggcag ttcatcctga gttctaagaa gctccttctc     300
agtgactctg gcttctatct ctgtgcctgg agttcaagcg gtttgggcgt tgagcagttc     360
ttcgggccag ggacacggct caccgtgcta gaggacctga aaacgtgtt cccacccgag     420
gtcgctgtgt ttgagccatc agaagcagag atctcccaca cccaaaaggc cacactggtg     480
tgcctggcca caggcttcta ccccgaccac gtggagctga gctggtgggt gaatgggaag     540
gaggtgcaca gtggggtcag cacagacccg cagcccctca aggagcagcc cgccctcaat     600
gactccagat actgcctgag cagccgcctg agggtctcgg ccaccttctg gcagaacccc     660
cgcaaccact tccgctgtca agtccagttc tacgggctct cggagaatga cgagtggacc     720
caggatagg ccaaacctgt cacccagatc gtcagcgccg aggcctgggg tagagcagac     780
tgtggcttca cctccgagtc ttaccagcaa ggggtcctgt ctgccaccat cctctatgag     840
atcttgctag gaaggccac cttgtatgcc gtgctggtca gtgccctcgt gctgatggcc     900
atggtcaaga gaaaggattc cagaggc                                        927
```

<210> SEQ ID NO 77
<211> LENGTH: 825
<212> TYPE: DNA
<213> ORGANISM: Artificial
<220> FEATURE:
<223> OTHER INFORMATION: survivin-directed TCR alpha-chain SW-Surv-22 alpha (VJ region)

<400> SEQUENCE: 77

```
atggagaaaa tgttggagtg tgcattcata gtcttgtggc ttcagcttgg ctggttgagt      60
ggagaagacc aggtgacgca gagtcccgag ccctgagac tccaggaggg agagagtagc     120
agtctcaact gcagttacac agtcagcggt ttaagagggc tgttctggta taggcaagat     180
cctgggaaag gccctgaatt cctcttcacc ctgtattcag ctgggaaga aaaggagaaa     240
gaaaggctaa agccacatt aacaaagaag gaaagctttc tgcacatcac agcccctaaa     300
cctgaagact cagccactta tctctgtgct gtgcaggctt actcaaattc gggtatgca     360
ctcaacttcg gcaaaggcac ctcgctgttg gtcacacccc atatccagaa ccctgaccct     420
gccgtgtacc agctgagaga ctctaaatcc agtgacaagt ctgtctgcct attcaccgat     480
tttgattctc aaacaaatgt gtcacaaagt aaggattctg atgtgtatat cacagacaaa     540
actgtgctag acatgaggtc tatggacttc aagagcaaca gtgctgtggc ctggagcaac     600
aaatctgact ttgcatgtgc aaacgccttc aacaacagca ttattccaga agacaccttc     660
ttcccccagcc cagaaagttc ctgtgatgtc aagctggtcg agaaaagctt tgaaacagat     720
acgaacctaa actttcaaaa cctgtcagtg attgggttcc gaatcctcct cctgaaagtg     780
```

```
gccgggttta atctgctcat gacgctgcgg ctgtggtcca gctga              825
```

<210> SEQ ID NO 78
<211> LENGTH: 912
<212> TYPE: DNA
<213> ORGANISM: Artificial
<220> FEATURE:
<223> OTHER INFORMATION: survivin-directed TCR alpha-chain SW-Surv-22
      beta (VDJ region)

<400> SEQUENCE: 78

```
atgctgagtc ttctgctcct tctcctggga ctaggctctg tgttcagtgc tgtcatctct   60
caaaagccaa gcagggatat ctgtcaacgt ggaacctccc tgacgatcca gtgtcaagtc  120
gatagccaag tcaccatgat gttctggtac cgtcagcaac ctggacagag cctgacactg  180
atcgcaactg caaatcaggg ctctgaggcc acatatgaga gtggatttgt cattgacaag  240
tttcccatca gccgcccaaa cctaacattc tcaactctga ctgtgagcaa catgagccct  300
gaagacagca gcatatatct ctgcagcgtt gaagacagct atggctacac cttcggttcg  360
gggaccaggt taaccgttgt agaggacctg aacaaggtgt tcccacccga ggtcgctgtg  420
tttgagccat cagaagcaga gatctcccac acccaaaagg ccacactggt gtgcctggcc  480
acaggcttct tccctgacca cgtggagctg agctggtggg tgaatgggaa ggaggtgcac  540
agtggggtca gcacggaccc gcagcccctc aaggagcagc cgccctcaa tgactccaga  600 tactgcctga gcagccgcct gagggtctcg gccaccttct ggcagaaccc ccgcaaccac  660
ttccgctgtc aagtccagtt ctacgggctc tcggagaatg acgagtggac ccaggatagg  720
gccaaacccg tcacccagat cgtcagcgcc gaggcctggg gtagagcaga ctgtggcttt  780
acctcggtgt cctaccagca aggggtcctg tctgccacca tcctctatga gatcctgcta  840
gggaaggcca ccctgtatgc tgtgctggtc agcgcccttg tgttgatggc catggtcaag  900
agaaaggatt tc                                                       912
```

<210> SEQ ID NO 79
<211> LENGTH: 813
<212> TYPE: DNA
<213> ORGANISM: Artificial
<220> FEATURE:
<223> OTHER INFORMATION: survivin-directed TCR alpha-chain SW-Surv-66
      alpha chain (VJ region)

<400> SEQUENCE: 79

```
atgacatcca ttcgagctgt atttatattc ctgtggctgc agctggactt ggtgaatgga   60
gagaatgtgg agcagcatcc ttcaaccctg agtgtccagg agggagacag cgctgttatc  120
aagtgtactt attcagacag tgcctcaaac tacttccctt ggtataagca agaacttgga  180
aaaagacctc agcttattat agacattcgt tcaaatgtgg gcgaaaagaa agaccaacga  240
attgctgtta cattgaacaa gacagccaaa catttctccc tgcacatcac agagacccaa  300
cctgaagact cggctgtcta cttctgtgca gcaagggcag gcaacatgct cacctttgga  360
gggggaacaa ggttaatggt caaaccccat atccagaacc ctgaccctgc cgtgtaccag  420
ctgagagact ctaaatccag tgacaagtct gtctgcctat tcaccgattt tgattctcaa  480
acaaatgtgt cacaaagtaa ggattctgat gtgtatatca cagacaaaac tgtgctagac  540
atgaggtcta tggacttcaa gagcaacagt gctgtggcct ggagcaacaa atctgacttt  600
gcatgtgcaa acgccttcaa caacagcatt attccagaag acaccttctt ccccagccca  660
```

```
gaaagttcct gtgatgtcaa gctggtcgag aaaagctttg aaacagatac gaacctaaac    720
tttcaaaacc tgtcagtgat tgggttccga atcctcctcc tgaaagtggc cgggtttaat    780
ctgctcatga cgctgcggct gtggtccagc tga                                 813
```

<210> SEQ ID NO 80
<211> LENGTH: 927
<212> TYPE: DNA
<213> ORGANISM: Artificial
<220> FEATURE:
<223> OTHER INFORMATION: survivin-directed TCR alpha-chain SW-Surv-66
      beta chain (VDJ region)

<400> SEQUENCE: 80

```
atgctctgct ctctccttgc ccttctcctg ggcactttct ttggggtcag atctcagact     60
attcatcaat ggccagcgac cctggtgcag cctgtgggca gcccgctctc tctggagtgc    120
actgtggagg gaacatcaaa ccccaaccta tactggtacc gacaggctgc aggcaggggc    180
ctccagctgc tcttctactc cgttggtatt ggccagatca gctctgaggt gcccagaat    240 ctctcagcct ccagacccca ggaccggcag ttcatcctga gttctaagaa gctccttctc    300
agtgactctg gcttctatct ctgtgcctgg ggtacgggac tagcgcttta cgagcagtac    360
ttcgggccgg gcaccaggct cacggtcaca gaggacctga aaaacgtgtt cccacccgag    420
gtcgctgtgt ttgagccatc agaagcagag atctcccaca cccaaaaggc cacactggtg    480
tgcctggcca caggcttcta ccccgaccac gtggagctga gctggtgggt gaatgggaag    540
gaggtgcaca gtgggtcag cacagaccg cagcccctca aggagcagcc cgccctcaat    600
gactccagat actgcctgag cagccgcctg agggtctcgg ccaccttctg gcagaacccc    660
cgcaaccact ccgctgtcca gtccagttc tacgggctct cggagaatga cgagtggacc    720
caggataggg ccaaacctgt cacccagatc gtcagcgccg aggcctgggg tagagcagac    780
tgtggcttca cctccgagtc ttaccagcaa ggggtcctgt ctgccaccat cctctatgag    840
atcttgctag ggaaggccac cttgtatgcc gtgctggtca gtgccctcgt gctgatggcc    900
atggtcaaga gaaaggattc cagaggc                                        927
```

<210> SEQ ID NO 81
<211> LENGTH: 813
<212> TYPE: DNA
<213> ORGANISM: Artificial
<220> FEATURE:
<223> OTHER INFORMATION: survivin-directed TCR alpha-chain SW-Surv-71
      alpha chain (VJ region)

<400> SEQUENCE: 81

```
atgaaatcct tgagagtttt actagtgatc ctgtggcttc agttgagctg ggtttggagc     60
caacagaagg aggtggagca gaattctgga cccctcagtg ttccagaggg agccattgcc    120
tctctcaact gcacttacag tgaccgaggt tcccagtcct tcttctggta cagacaatat    180
tctgggaaaa gccctgagtt gataatgttc atatactcca atggtgacaa agaagatgga    240
aggtttacag cacagctcaa taaagccagc cagtatgttt ctctgctcat cagagactcc    300
cagcccagtg attcagccac ctacctctgt gccgtgaaca atgccagact catgtttgga    360
gatggaactc agctggtggt gaagcccaat atccagaacc ctgaccctgc cgtgtaccag    420
ctgagagact ctaaatccag tgacaagtct gtctgcctat tcaccgattt tgattctcaa    480
acaaatgtgt cacaaagtaa ggattctgat gtgtatatca cagacaaaac tgtgctagac    540
atgaggtcta tggacttcaa gagcaacagt gctgtggcct ggagcaacaa atctgacttt    600
```

```
gcatgtgcaa acgccttcaa caacagcatt attccagaag acaccttctt ccccagccca    660
gaaagttcct gtgatgtcaa gctggtcgag aaaagctttg aaacagatac gaacctaaac    720
tttcaaaacc tgtcagtgat tgggttccga atcctcctcc tgaaagtggc cgggttaat    780 ctgctcatga cgctgcggct gtggtccagc tga                                 813
```

<210> SEQ ID NO 82
<211> LENGTH: 918
<212> TYPE: DNA
<213> ORGANISM: Artificial
<220> FEATURE:
<223> OTHER INFORMATION: survivin-directed TCR alpha-chain SW-Surv-71
      beta chain (VDJ region)

<400> SEQUENCE: 82

```
atgctctgct ctctccttgc ccttctcctg ggcactttct ttggggtcag atctcagact     60
attcatcaat ggccagcgac cctggtgcag cctgtgggca gcccgctctc tctggagtgc    120
actgtggagg gaacatcaaa ccccaaccta tactggtacc gacaggctgc aggcaggggc    180
ctccagctgc tcttctactc cgttggtatt ggccagatca gctctgaggt gccccagaat    240
ctctcagcct ccagacccca ggaccggcag ttcatcctga gttctaagaa gctccttctc    300
agtgactctg gcttctatct ctgtgcctgg agcataggcg ctgagcagtt cttcgggcca    360
gggacacggc tcaccgtgct agaggacctg aaaaacgtgt tcccaccccga ggtcgctgtg    420 tttgagccat cagaagcaga gatctcccac acccaaaagg ccacactggt gtgcctggcc    480
acaggcttct accccgacca cgtggagctg agctggtggg tgaatgggaa ggaggtgcac    540
agtggggtca gcacagaccc gcagcccctc aaggagcagc ccgccctcaa tgactccaga    600
tactgcctga gcagccgcct gagggtctcg gccaccttct ggcagaaccc ccgcaaccac    660
ttccgctgtc aagtccagtt ctacgggctc tcggagaatg acgagtggac ccaggatagg    720
gccaaacctg tcacccagat cgtcagcgcc gaggcctggg gtagagcaga ctgtggcttc    780
acctccgagt cttaccagca aggggtcctg tctgccacca tcctctatga gatcttgcta    840
gggaaggcca ccttgtatgc cgtgctggtc agtgccctcg tgctgatggc catggtcaag    900
agaaaggatt ccagaggc                                                  918
```

<210> SEQ ID NO 83
<211> LENGTH: 831
<212> TYPE: DNA
<213> ORGANISM: Artificial
<220> FEATURE:
<223> OTHER INFORMATION: survivin-directed TCR alpha-chain SW-Surv-72
      alpha chain (VJ region)

<400> SEQUENCE: 83

```
atgtcacttt ctagcctgct gaaggtggtc acagcttcac tgtggctagg acctggcatt     60
gcccagaaga taactcaaac ccaaccagga atgttcgtgc aggaaaagga ggctgtgact    120
ctggactgca catatgacac cagtgatcaa agttatggtc tattctggta caagcagccc    180
agcagtgggg aaatgatttt tcttatttat caggggtctt atgacgagca aaatgcaaca    240
gaaggtcgct actcattgaa tttccagaag gcaagaaaat ccgccaacct tgtcatctcc    300
gcttcacaac tgggggactc agcaatgtat ttctgtgcaa tgagagaggg cggggctac    360 aataagctga ttttggagc agggaccagg ctggctgtac acccatatat ccagaaccct    420
gaccctgccg tgtaccagct gagagactct aaatccagtg acaagtctgt ctgcctattc    480
```

```
accgattttg attctcaaac aaatgtgtca caaagtaagg attctgatgt gtatatcaca    540
gacaaaactg tgctagacat gaggtctatg gacttcaaga gcaacagtgc tgtggcctgg    600
agcaacaaat ctgactttgc atgtgcaaac gccttcaaca acagcattat tccagaagac    660
accttcttcc ccagcccaga aagttcctgt gatgtcaagc tggtcgagaa aagctttgaa    720
acagatacga acctaaactt tcaaaacctg tcagtgattg ggttccgaat cctcctcctg    780
aaagtggccg ggtttaatct gctcatgacg ctgcggctgt ggtccagctg a             831
```

<210> SEQ ID NO 84
<211> LENGTH: 915
<212> TYPE: DNA
<213> ORGANISM: Artificial
<220> FEATURE:
<223> OTHER INFORMATION: survivin-directed TCR alpha-chain SW-Surv-72
      beta chain (VDJ region)

<400> SEQUENCE: 84

```
atgctctgct ctctccttgc ccttctcctg ggcactttct ttggggtcag atctcagact     60
attcatcaat ggccagcgac cctggtgcag cctgtgggca gcccgctctc tctggagtgc    120
actgtggagg gaacatcaaa ccccaaccta tactggtacc gacaggctgc aggcaggggc    180
ctccagctgc tcttctactc cgttggtatt ggccagatca gctctgaggt gccccagaat    240
ctctcagcct ccagacccca ggaccggcag ttcatcctga ttctaagaa gctcctcctc     300 agtgactctg gcttctatct ctgtgccgga caggatttga acactgaagc tttctttgga    360
caaggcacca gactcacagt tgtagaggac ctgaacaagg tgttcccacc cgaggtcgct    420
gtgtttgagc catcagaagc agagatctcc cacacccaaa aggccacact ggtgtgcctg    480
gccacaggct tcttccctga ccacgtggag ctgagctggt gggtgaatgg gaaggaggtg    540
cacagtgggg tcagcacgga cccgcagccc tcaaggagc agcccgccct caatgactcc     600
agatactgcc tgagcagccg cctgagggtc tcggccacct tctggcagaa cccccgcaac    660
cacttccgct gtcaagtcca gttctacggg ctctcggaga tgacgagtg gacccaggat     720 agggccaaac ccgtcaccca gatcgtcagc gccgaggcct ggggtagagc agactgtggc    780
tttacctcgg tgtcctacca gcaaggggtc ctgtctgcca ccatcctcta tgagatcctg    840
ctagggaagg ccaccctgta tgctgtgctg gtcagcgccc ttgtgttgat ggccatggtc    900
aagagaaagg atttc                                                     915
```

<210> SEQ ID NO 85
<211> LENGTH: 9
<212> TYPE: PRT
<213> ORGANISM: Artificial
<220> FEATURE:
<223> OTHER INFORMATION: synthetic tyrosinase peptide YMD,
      tyrosinase-369-377

<400> SEQUENCE: 85

Tyr Met Asp Gly Thr Met Ser Gln Val
1               5

<210> SEQ ID NO 86
<211> LENGTH: 10
<212> TYPE: PRT
<213> ORGANISM: Artificial
<220> FEATURE:
<223> OTHER INFORMATION: synthetic Melan-A peptide ELA, melan-A-27-35

<400> SEQUENCE: 86

```
Glu Leu Ala Gly Ile Gly Ile Leu Thr Val
1               5                   10

<210> SEQ ID NO 87
<211> LENGTH: 9
<212> TYPE: PRT
<213> ORGANISM: Artificial
<220> FEATURE:
<223> OTHER INFORMATION: synthetic survivin peptide LML, survivin-96-104

<400> SEQUENCE: 87

Leu Met Leu Gly Glu Phe Leu Lys Leu
1               5

<210> SEQ ID NO 88
<211> LENGTH: 8
<212> TYPE: PRT
<213> ORGANISM: Artificial
<220> FEATURE:
<223> OTHER INFORMATION: synthetic influenza peptide GIL control,
      influenza matrix protein-58-66

<400> SEQUENCE: 88

Gly Ile Leu Gly Phe Val Thr Leu
1               5
```